US012427249B2

(12) United States Patent
Chaya et al.

(10) Patent No.: US 12,427,249 B2
(45) Date of Patent: Sep. 30, 2025

(54) FLUID INJECTOR SYSTEM WITH IMPROVED RATIO PERFORMANCE

(71) Applicant: BAYER HEALTHCARE LLC, Whippany, NJ (US)

(72) Inventors: Amy Chaya, Strafford, PA (US); Michael Spohn, Fenelton, PA (US); Michael McDermott, Pittsburgh, PA (US); William Barone, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 1156 days.

(21) Appl. No.: 17/270,616

(22) PCT Filed: Aug. 27, 2019

(86) PCT No.: PCT/US2019/048276
§ 371 (c)(1),
(2) Date: Feb. 23, 2021

(87) PCT Pub. No.: WO2020/046889
PCT Pub. Date: Mar. 5, 2020

(65) Prior Publication Data
US 2021/0220557 A1    Jul. 22, 2021

Related U.S. Application Data

(60) Provisional application No. 62/723,724, filed on Aug. 28, 2018.

(51) Int. Cl.
*A61M 5/168*    (2006.01)
*A61M 5/14*    (2006.01)
*A61M 5/142*    (2006.01)

(52) U.S. Cl.
CPC ...... *A61M 5/16827* (2013.01); *A61M 5/1408* (2013.01); *A61M 5/1422* (2013.01);
(Continued)

(58) Field of Classification Search
CPC ............ A61M 5/16827; A61M 5/1408; A61M 5/1407; A61M 5/1422; A61M 5/14216;
(Continued)

(56) References Cited

U.S. PATENT DOCUMENTS 383,858 A    6/1888 Campbell
508,584 A    11/1893 Stevens
(Continued)

FOREIGN PATENT DOCUMENTS

CA    2045070 A1    2/1992
CA    2077712 A1    12/1993
(Continued)

OTHER PUBLICATIONS

The International Preliminary Report on Patentability and Written Opinion mailed on Sep. 24, 2015 from corresponding PCT Application No. PCT/US2014/026324.
(Continued)

*Primary Examiner* — Kevin C Sirmons
*Assistant Examiner* — Alexandra Lalonde
(74) *Attorney, Agent, or Firm* — Joseph L. Kent; Alexandria Quezada; James R. Stevenson

(57) ABSTRACT

A fluid injector system includes a control device operatively associated with a first drive component configured to pressurize and inject a first fluid and a second drive component configured to pressurize and inject a second fluid. The control device includes at least one processor programmed or configured to: during a first phase of a multi-phase injection protocol, actuate at least the first drive component to inject the first fluid; during the first phase of the multi-
(Continued)

phase injection protocol and prior to transitioning to a second phase of the multi-phase injection protocol, actuate the second drive component to pressurize the second fluid relative to a pressure of the first fluid; and during the second phase of the multi-phase injection protocol, actuate the second drive component to inject at least the second fluid so that a desired steady-state ratio of the first fluid and the second fluid in the second phase is reached.

14 Claims, 9 Drawing Sheets

(52) U.S. Cl.
CPC ............ *A61M 2005/14208* (2013.01); *A61M 2205/52* (2013.01)

(58) Field of Classification Search
CPC ........ A61M 5/142; A61M 2005/14208; A61M 2205/52; A61M 2039/0027; A61M 2039/1077; A61M 39/105
See application file for complete search history.

(56) References Cited

U.S. PATENT DOCUMENTS

| | | |
|---|---|---|
| 945,143 A | 1/1910 | Iacques |
| 2,511,291 A | 6/1950 | Mueller |
| 2,583,206 A | 1/1952 | Borck et al. |
| 3,156,236 A | 11/1964 | Williamson |
| 3,159,312 A | 12/1964 | Van Sciver, II |
| 3,276,472 A | 10/1966 | Jinkens et al. |
| 3,349,713 A | 10/1967 | Fassbender |
| 3,520,295 A | 7/1970 | Paul |
| 3,523,523 A | 8/1970 | Heinrich et al. |
| 3,623,474 A | 11/1971 | Heilman et al. |
| 3,635,444 A | 1/1972 | Potter |
| 3,671,208 A | 6/1972 | Wayne |
| 3,701,345 A | 10/1972 | Heilman |
| 3,719,207 A | 3/1973 | Takeda |
| 3,755,655 A | 8/1973 | Senecal |
| 3,769,976 A | 11/1973 | Victory |
| 3,793,600 A | 2/1974 | Grosbard |
| 3,812,843 A | 5/1974 | Wootten et al. |
| 3,817,843 A | 6/1974 | Barrett |
| 3,839,708 A | 10/1974 | Lyons et al. |
| 3,868,967 A | 3/1975 | Harding |
| 3,888,239 A | 6/1975 | Rubinstein |
| 3,895,220 A | 7/1975 | Nelson et al. |
| 3,898,983 A | 8/1975 | Elam |
| 3,927,955 A | 12/1975 | Spinosa et al. |
| 3,941,126 A | 3/1976 | Dietrich et al. |
| 3,958,103 A | 5/1976 | Oka et al. |
| 3,968,195 A | 7/1976 | Bishop |
| 3,995,381 A | 12/1976 | Manfred et al. |
| 4,001,549 A | 1/1977 | Corwin |
| 4,006,736 A | 2/1977 | Kranys et al. |
| 4,038,981 A | 8/1977 | Lefevre et al. |
| 4,044,757 A | 8/1977 | Mcwhorter et al. |
| 4,090,502 A | 5/1978 | Tajika |
| 4,135,247 A | 1/1979 | Gordon et al. |
| 4,151,845 A | 5/1979 | Clemens |
| 4,187,057 A | 2/1980 | Xanthopoulos |
| 4,191,183 A | 3/1980 | Mendelson |
| 4,199,000 A | 4/1980 | Edstrom |
| 4,204,775 A | 5/1980 | Speer |
| 4,207,871 A | 6/1980 | Jenkins |
| 4,208,136 A | 6/1980 | King et al. |
| 4,223,675 A | 9/1980 | Williams |
| 4,262,824 A | 4/1981 | Hrynewycz |
| 4,263,916 A | 4/1981 | Brooks et al. |
| 4,280,494 A | 7/1981 | Cosgrove, Jr. et al. |
| 4,284,073 A | 8/1981 | Krause et al. |
| 4,315,247 A | 2/1982 | Germanton |
| 4,319,568 A | 3/1982 | Tregoning |
| 4,329,067 A | 5/1982 | Goudy, Jr. |
| 4,340,153 A | 7/1982 | Spivey |
| 4,341,153 A | 7/1982 | Bowser |
| 4,392,847 A | 7/1983 | Whitney et al. |
| 4,392,849 A | 7/1983 | Petre et al. |
| 4,396,385 A | 8/1983 | Kelly et al. |
| 4,402,310 A | 9/1983 | Kimura |
| 4,409,966 A | 10/1983 | Lambrecht et al. |
| 4,434,820 A | 3/1984 | Glass |
| 4,434,822 A | 3/1984 | Bellamy et al. |
| 4,441,823 A | 4/1984 | Power et al. |
| 4,444,198 A | 4/1984 | Petre |
| 4,447,230 A | 5/1984 | Gula et al. |
| 4,448,200 A | 5/1984 | Brooks et al. |
| 4,474,476 A | 10/1984 | Thomsen |
| 4,477,923 A | 10/1984 | Baumann et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,504,908 A | 3/1985 | Riederer et al. |
| 4,509,526 A | 4/1985 | Barnes et al. |
| 4,512,764 A | 4/1985 | Wunsch |
| 4,542,459 A | 9/1985 | Riederer |
| 4,544,949 A | 10/1985 | Kurihara |
| 4,551,133 A | 11/1985 | Zegers et al. |
| 4,552,130 A | 11/1985 | Kinoshita |
| 4,559,036 A | 12/1985 | Wunsch |
| 4,563,175 A | 1/1986 | Lafond |
| 4,578,802 A | 3/1986 | Itoh |
| 4,585,009 A | 4/1986 | Barker et al. |
| 4,585,941 A | 4/1986 | Bergner |
| 4,610,665 A | 9/1986 | Matsumoto et al. |
| 4,610,670 A | 9/1986 | Spencer |
| 4,610,790 A | 9/1986 | Reti et al. |
| 4,611,340 A | 9/1986 | Okazaki |
| 4,612,572 A | 9/1986 | Komatsu et al. |
| 4,625,494 A | 12/1986 | Iwatschenko et al. |
| 4,626,144 A | 12/1986 | Berner |
| 4,633,307 A | 12/1986 | Honda |
| 4,634,426 A | 1/1987 | Kamen |
| 4,636,144 A | 1/1987 | Abe et al. |
| 4,655,197 A | 4/1987 | Atkinson |
| 4,662,906 A | 5/1987 | Matkovich et al. |
| 4,672,651 A | 6/1987 | Horiba et al. |
| 4,676,776 A | 6/1987 | Howson |
| 4,682,170 A | 7/1987 | Kubota et al. |
| 4,689,670 A | 8/1987 | Okazaki |
| 4,710,166 A | 12/1987 | Thompson et al. |
| 4,723,261 A | 2/1988 | Janssen et al. |
| 4,750,643 A | 6/1988 | Wortrich |
| 4,754,786 A | 7/1988 | Roberts |
| 4,781,687 A | 11/1988 | Wall |
| 4,783,273 A | 11/1988 | Knutsson et al. |
| 4,789,014 A | 12/1988 | Digianfilippo et al. |
| 4,793,357 A | 12/1988 | Lindstrom |
| 4,795,429 A | 1/1989 | Feldstein |
| 4,798,590 A | 1/1989 | O'Leary et al. |
| 4,804,454 A | 2/1989 | Asakura et al. |
| 4,823,833 A | 4/1989 | Hogan et al. |
| 4,835,521 A | 5/1989 | Andrejasich et al. |
| 4,836,187 A | 6/1989 | Iwakoshi et al. |
| 4,838,856 A | 6/1989 | Mulreany et al. |
| 4,840,620 A | 6/1989 | Kobayashi et al. |
| 4,844,052 A | 7/1989 | Iwakoshi et al. |
| 4,853,521 A | 8/1989 | Claeys et al. |
| 4,854,301 A | 8/1989 | Nakajima |
| 4,854,324 A | 8/1989 | Hirschman et al. |
| 4,857,056 A | 8/1989 | Talonn |
| 4,874,359 A | 10/1989 | White et al. |
| 4,879,880 A | 11/1989 | Harrison |
| 4,880,014 A | 11/1989 | Zarowitz et al. |
| 4,887,208 A | 12/1989 | Schneider et al. |
| 4,887,554 A | 12/1989 | Whitford |
| 4,901,731 A | 2/1990 | Millar |
| 4,903,705 A | 2/1990 | Imamura et al. |
| 4,913,154 A | 4/1990 | Ermert et al. |
| 4,922,916 A | 5/1990 | Ermert et al. |
| 4,925,444 A | 5/1990 | Orkin et al. |

(56) References Cited

U.S. PATENT DOCUMENTS

| | | |
|---|---|---|
| 4,929,818 A | 5/1990 | Bradbury et al. |
| 4,935,005 A | 6/1990 | Haines |
| 4,936,832 A | 6/1990 | Vaillancourt |
| 4,943,279 A | 7/1990 | Samiotes et al. |
| 4,943,779 A | 7/1990 | Pedersen et al. |
| 4,943,987 A | 7/1990 | Asahina et al. |
| 4,946,256 A | 8/1990 | Woodruff |
| 4,946,439 A | 8/1990 | Eggers |
| 4,947,412 A | 8/1990 | Mattson |
| 4,950,245 A | 8/1990 | Brown et al. |
| 4,952,068 A | 8/1990 | Flint |
| 4,954,129 A | 9/1990 | Giuliani et al. |
| 4,965,726 A | 10/1990 | Heuscher et al. |
| 4,966,579 A | 10/1990 | Polaschegg |
| 4,976,687 A | 12/1990 | Martin |
| 4,978,335 A | 12/1990 | Arthur, III |
| 4,981,467 A | 1/1991 | Bobo, Jr. et al. |
| 4,995,064 A | 2/1991 | Wilson et al. |
| 5,002,055 A | 3/1991 | Merki et al. |
| 5,004,472 A | 4/1991 | Wallace et al. |
| 5,009,654 A | 4/1991 | Minshall et al. |
| 5,010,473 A | 4/1991 | Jacobs |
| 5,013,173 A | 5/1991 | Shiraishi |
| 5,018,173 A | 5/1991 | Komai et al. |
| 5,026,348 A | 6/1991 | Venegas |
| 5,032,112 A | 7/1991 | Fairchild et al. |
| 5,034,987 A | 7/1991 | Fujimoto et al. |
| 5,040,537 A | 8/1991 | Katakura |
| 5,053,002 A | 10/1991 | Barlow |
| 5,054,044 A | 10/1991 | Audon et al. |
| 5,056,568 A | 10/1991 | Digianfilippo et al. |
| 5,059,171 A | 10/1991 | Bridge et al. |
| 5,059,173 A | 10/1991 | Sacco |
| 5,061,243 A | 10/1991 | Winchell et al. |
| 5,069,662 A | 12/1991 | Bodden |
| 5,078,683 A | 1/1992 | Sancoff et al. |
| 5,088,981 A | 2/1992 | Howson et al. |
| 5,100,380 A | 3/1992 | Epstein et al. |
| 5,104,374 A | 4/1992 | Bishko et al. |
| 5,104,387 A | 4/1992 | Pokorney et al. |
| 5,108,365 A | 4/1992 | Woods, Jr. |
| 5,111,492 A | 5/1992 | Klausz |
| 5,113,905 A | 5/1992 | Pruitt et al. |
| 5,123,056 A | 6/1992 | Wilson |
| 5,123,121 A | 6/1992 | Broersma |
| 5,125,018 A | 6/1992 | Asahina |
| 5,128,121 A | 7/1992 | Berg et al. |
| 5,133,336 A | 7/1992 | Savitt et al. |
| 5,135,000 A | 8/1992 | Akselrod et al. |
| 5,140,862 A | 8/1992 | Pappalardo |
| 5,150,292 A | 9/1992 | Hoffmann et al. |
| 5,163,928 A | 11/1992 | Hobbs et al. |
| 5,166,961 A | 11/1992 | Brunnett et al. |
| 5,180,895 A | 1/1993 | Briggs et al. |
| 5,180,896 A | 1/1993 | Gibby et al. |
| 5,190,744 A | 3/1993 | Rocklage et al. |
| 5,191,878 A | 3/1993 | Iida et al. |
| 5,196,007 A | 3/1993 | Ellman et al. |
| 5,199,604 A | 4/1993 | Palmer et al. |
| 5,207,642 A | 5/1993 | Orkin et al. |
| 5,215,095 A | 6/1993 | Macvicar et al. |
| 5,228,070 A | 7/1993 | Mattson |
| 5,230,614 A | 7/1993 | Zanger et al. |
| 5,242,390 A | 9/1993 | Goldrath |
| 5,249,122 A | 9/1993 | Stritzke |
| 5,249,579 A | 10/1993 | Hobbs et al. |
| 5,262,946 A | 11/1993 | Heuscher |
| 5,267,174 A | 11/1993 | Kaufman et al. |
| 5,269,756 A | 12/1993 | Dryden |
| 5,273,537 A | 12/1993 | Haskvitz et al. |
| 5,274,218 A | 12/1993 | Urata et al. |
| 5,276,614 A | 1/1994 | Heuscher |
| 5,286,252 A | 2/1994 | Tuttle et al. |
| 5,287,273 A | 2/1994 | Kupfer et al. |
| 5,295,967 A | 3/1994 | Rondelet et al. |
| 5,300,031 A | 4/1994 | Neer et al. |
| 5,301,656 A | 4/1994 | Negoro et al. |
| 5,301,672 A | 4/1994 | Kalender |
| 5,304,126 A | 4/1994 | Epstein et al. |
| 5,310,997 A | 5/1994 | Roach et al. |
| 5,311,568 A | 5/1994 | Mckee, Jr. et al. |
| 5,313,992 A | 5/1994 | Grabenkort |
| 5,317,506 A | 5/1994 | Coutre et al. |
| 5,328,463 A | 7/1994 | Barton et al. |
| 5,329,459 A | 7/1994 | Kaufman et al. |
| 5,334,141 A | 8/1994 | Carr et al. |
| 5,339,799 A | 8/1994 | Kami et al. |
| 5,349,625 A | 9/1994 | Born et al. |
| 5,349,635 A | 9/1994 | Scott |
| 5,352,979 A | 10/1994 | Conturo |
| 5,354,273 A | 10/1994 | Hagen |
| 5,361,761 A | 11/1994 | Van et al. |
| 5,362,948 A | 11/1994 | Morimoto |
| 5,368,562 A | 11/1994 | Blomquist et al. |
| 5,368,567 A | 11/1994 | Lee |
| 5,368,570 A | 11/1994 | Thompson et al. |
| 5,373,231 A | 12/1994 | Boll et al. |
| 5,376,070 A | 12/1994 | Purvis et al. |
| 5,378,231 A | 1/1995 | Johnson et al. |
| 5,382,232 A | 1/1995 | Hague et al. |
| 5,383,231 A | 1/1995 | Yamagishi |
| 5,383,858 A | 1/1995 | Reilly et al. |
| 5,385,540 A | 1/1995 | Abbott et al. |
| 5,388,139 A | 2/1995 | Beland |
| 5,392,849 A | 2/1995 | Matsunaga et al. |
| 5,400,792 A | 3/1995 | Hoebel et al. |
| 5,417,213 A | 5/1995 | Prince |
| 5,431,627 A | 7/1995 | Pastrone et al. |
| 5,433,704 A | 7/1995 | Ross et al. |
| 5,445,621 A | 8/1995 | Poli et al. |
| 5,450,847 A | 9/1995 | Kaempfe et al. |
| 5,453,639 A | 9/1995 | Cronin et al. |
| 5,456,255 A | 10/1995 | Abe et al. |
| 5,458,128 A | 10/1995 | Polanyi et al. |
| 5,459,769 A | 10/1995 | Brown |
| 5,460,609 A | 10/1995 | O'Donnell |
| 5,464,391 A | 11/1995 | Devale |
| 5,468,240 A | 11/1995 | Gentelia et al. |
| 5,469,769 A | 11/1995 | Sawada et al. |
| 5,469,849 A | 11/1995 | Sasaki et al. |
| 5,472,403 A | 12/1995 | Cornacchia et al. |
| 5,474,683 A | 12/1995 | Bryant et al. |
| 5,485,831 A | 1/1996 | Holdsworth et al. |
| 5,489,265 A | 2/1996 | Montalvo et al. |
| 5,494,036 A | 2/1996 | Uber, III et al. |
| 5,494,822 A | 2/1996 | Sadri |
| 5,496,273 A | 3/1996 | Pastrone et al. |
| 5,507,412 A | 4/1996 | Ebert et al. |
| 5,515,851 A | 5/1996 | Goldstein |
| 5,522,798 A | 6/1996 | Johnson et al. |
| 5,531,679 A | 7/1996 | Schulman et al. |
| 5,531,697 A | 7/1996 | Olsen et al. |
| 5,533,978 A | 7/1996 | Teirstein |
| 5,544,215 A | 8/1996 | Shroy, Jr. et al. |
| 5,547,470 A | 8/1996 | Johnson et al. |
| 5,552,130 A | 9/1996 | Kraus et al. |
| 5,553,619 A | 9/1996 | Prince |
| 5,560,317 A | 10/1996 | Bunyan et al. |
| 5,566,092 A | 10/1996 | Wang et al. |
| 5,569,181 A | 10/1996 | Heilman et al. |
| 5,569,208 A | 10/1996 | Woelpper et al. |
| 5,573,515 A | 11/1996 | Wilson et al. |
| 5,579,767 A | 12/1996 | Prince |
| 5,583,902 A | 12/1996 | Bae |
| 5,590,654 A | 1/1997 | Prince |
| 5,592,940 A | 1/1997 | Kampfe et al. |
| 5,601,086 A | 2/1997 | Pretlow, III et al. |
| 5,611,344 A | 3/1997 | Bernstein et al. |
| 5,616,124 A | 4/1997 | Hague et al. |
| 5,651,776 A | 7/1997 | Appling et al. |
| 5,681,285 A | 10/1997 | Ford et al. |
| 5,687,208 A | 11/1997 | Bae et al. |
| 5,687,708 A | 11/1997 | Farnsworth et al. |
| 5,713,358 A | 2/1998 | Mistretta et al. |

(56) References Cited

U.S. PATENT DOCUMENTS

| | | |
|---|---|---|
| 5,724,976 A | 3/1998 | Mine et al. |
| 5,725,500 A | 3/1998 | Micheler |
| 5,739,508 A | 4/1998 | Uber, III |
| 5,743,266 A | 4/1998 | Levene et al. |
| 5,768,405 A | 6/1998 | Makram-Ebeid |
| 5,796,862 A | 8/1998 | Pawlicki et al. |
| 5,799,649 A | 9/1998 | Prince |
| 5,800,397 A | 9/1998 | Wilson et al. |
| 5,806,519 A | 9/1998 | Evans, III et al. |
| 5,808,203 A | 9/1998 | Nolan, Jr. et al. |
| 5,827,219 A | 10/1998 | Uber, III et al. |
| 5,827,504 A | 10/1998 | Yan et al. |
| 5,840,026 A | 11/1998 | Uber, III et al. |
| 5,843,037 A | 12/1998 | Uber, III |
| 5,846,517 A | 12/1998 | Unger |
| 5,865,744 A | 2/1999 | Lemelson |
| 5,873,861 A | 2/1999 | Hitchins et al. |
| 5,881,124 A | 3/1999 | Giger et al. |
| 5,882,343 A | 3/1999 | Wilson et al. |
| 5,902,054 A | 5/1999 | Coudray |
| 5,903,454 A | 5/1999 | Hoffberg et al. |
| 5,916,165 A | 6/1999 | Duchon et al. |
| 5,920,054 A | 7/1999 | Uber |
| 5,947,935 A | 9/1999 | Kazousky et al. |
| 5,954,668 A | 9/1999 | Uber, III et al. |
| 5,964,703 A | 10/1999 | Goodman et al. |
| 5,987,347 A | 11/1999 | Khoury et al. |
| 5,988,587 A | 11/1999 | Duchon et al. |
| 6,046,225 A | 4/2000 | Maddock |
| 6,055,985 A | 5/2000 | Bae et al. |
| 6,056,902 A | 5/2000 | Hettinga |
| 6,063,052 A | 5/2000 | Uber, III et al. |
| 6,073,042 A | 6/2000 | Simonetti |
| 6,099,502 A | 8/2000 | Duchon et al. |
| 6,113,568 A | 9/2000 | Olaussen |
| 6,132,396 A | 10/2000 | Antanavich et al. |
| 6,149,627 A | 11/2000 | Uber, III |
| 6,159,183 A | 12/2000 | Neer et al. |
| 6,186,146 B1 | 2/2001 | Glickman |
| 6,201,889 B1 | 3/2001 | Vannah |
| 6,221,045 B1 | 4/2001 | Duchon et al. |
| 6,236,706 B1 | 5/2001 | Hsieh |
| 6,248,093 B1 | 6/2001 | Moberg |
| 6,306,117 B1 | 10/2001 | Uber, III |
| 6,313,131 B1 | 11/2001 | Lawyer |
| 6,317,623 B1 | 11/2001 | Griffiths et al. |
| 6,322,535 B1 | 11/2001 | Hitchins et al. |
| 6,344,030 B1 | 2/2002 | Duchon et al. |
| 6,375,624 B1 | 4/2002 | Uber, III et al. |
| 6,381,486 B1 | 4/2002 | Mistretta et al. |
| 6,387,098 B1 | 5/2002 | Cole et al. |
| 6,397,093 B1 | 5/2002 | Aldrich |
| 6,397,097 B1 | 5/2002 | Requardt |
| 6,402,697 B1 | 6/2002 | Calkins et al. |
| 6,408,204 B1 | 6/2002 | Hirschman |
| 6,423,719 B1 | 7/2002 | Lawyer |
| 6,442,418 B1 | 8/2002 | Evans, III et al. |
| 6,459,931 B1 | 10/2002 | Hirschman |
| 6,470,889 B1 | 10/2002 | Bae et al. |
| 6,471,674 B1 | 10/2002 | Emig et al. |
| 6,478,735 B1 | 11/2002 | Pope et al. |
| 6,503,226 B1 | 1/2003 | Martinell et al. |
| 6,520,930 B2 | 2/2003 | Critchlow et al. |
| 6,527,718 B1 | 3/2003 | Connor et al. |
| 6,554,819 B2 | 4/2003 | Reich |
| 6,556,695 B1 | 4/2003 | Packer et al. |
| 6,572,851 B2 | 6/2003 | Muramatsu et al. |
| 6,574,496 B1 | 6/2003 | Golman et al. |
| 6,575,930 B1 | 6/2003 | Trombley, III et al. |
| 6,597,938 B2 | 7/2003 | Liu |
| 6,626,862 B1 | 9/2003 | Duchon et al. |
| 6,635,030 B1 | 10/2003 | Bae et al. |
| 6,643,537 B1 | 11/2003 | Zatezalo et al. |
| 6,652,489 B2 | 11/2003 | Trocki et al. |
| 6,656,157 B1 | 12/2003 | Duchon et al. |
| 6,673,033 B1 | 1/2004 | Sciulli et al. |
| 6,685,733 B1 | 2/2004 | Dae et al. |
| 6,691,047 B1 | 2/2004 | Fredericks |
| 6,699,219 B2 | 3/2004 | Emig et al. |
| 6,731,971 B2 | 5/2004 | Evans et al. |
| 6,751,500 B2 | 6/2004 | Hirschman |
| 6,754,521 B2 | 6/2004 | Prince |
| 6,775,764 B1 | 8/2004 | Batcher |
| 6,776,764 B2 | 8/2004 | Pinsky |
| 6,866,653 B2 | 3/2005 | Bae |
| 6,876,720 B2 | 4/2005 | Tsuyuki |
| 6,879,853 B2 | 4/2005 | Meaney et al. |
| 6,983,590 B2 | 1/2006 | Roelle et al. |
| 7,047,058 B1 | 5/2006 | Dvorsky et al. |
| 7,094,216 B2 | 8/2006 | Trombley, III et al. |
| 7,122,012 B2 | 10/2006 | Bouton et al. |
| 7,267,666 B1 | 9/2007 | Duchon et al. |
| 7,267,667 B2 | 9/2007 | Houde et al. |
| 7,292,720 B2 | 11/2007 | Horger et al. |
| 7,351,221 B2 | 4/2008 | Trombley et al. |
| 7,427,281 B2 | 9/2008 | Uber et al. |
| 7,553,294 B2 | 6/2009 | Lazzaro et al. |
| 7,553,295 B2 | 6/2009 | Susi |
| 7,556,619 B2 | 7/2009 | Spohn et al. |
| 7,563,249 B2 | 7/2009 | Schriver et al. |
| 7,591,792 B2 | 9/2009 | Bouton |
| 7,666,169 B2 | 2/2010 | Cowan et al. |
| 7,688,057 B2 | 3/2010 | Foss et al. |
| 7,766,883 B2 | 8/2010 | Reilly et al. |
| 7,861,893 B2 | 1/2011 | Voegele et al. |
| 7,925,330 B2 | 4/2011 | Kalafut et al. |
| 7,937,134 B2 | 5/2011 | Uber et al. |
| 8,007,487 B2 | 8/2011 | Patrick et al. |
| 8,057,406 B2 | 11/2011 | Mohiuddin |
| 8,147,464 B2 | 4/2012 | Spohn et al. |
| 8,162,903 B2 | 4/2012 | Reilly et al. |
| 8,235,949 B2 | 8/2012 | Hack et al. |
| 8,295,914 B2 | 10/2012 | Kalafut et al. |
| 8,295,920 B2 | 10/2012 | Bouton et al. |
| 8,337,456 B2 | 12/2012 | Schriver et al. |
| 8,377,003 B2 | 2/2013 | Wagner |
| 8,403,909 B2 | 3/2013 | Spohn et al. |
| 8,439,863 B2 | 5/2013 | Fago et al. |
| 8,486,017 B2 | 7/2013 | Masuda et al. |
| 8,540,698 B2 | 9/2013 | Spohn et al. |
| 8,905,969 B2 | 12/2014 | Nystrom et al. |
| 8,945,051 B2 | 2/2015 | Schriver et al. |
| 9,101,708 B2 | 8/2015 | Small et al. |
| 9,173,995 B1 | 11/2015 | Tucker et al. |
| 9,199,033 B1 | 12/2015 | Cowan et al. |
| 9,238,099 B2 | 1/2016 | Kalafut et al. |
| 9,242,083 B2 | 1/2016 | Fago et al. |
| 9,259,527 B2 | 2/2016 | Spohn et al. |
| 9,289,550 B1 | 3/2016 | Dvorsky et al. |
| 9,314,749 B2 | 4/2016 | Yagi et al. |
| 9,326,686 B2 | 5/2016 | Warren et al. |
| 9,333,293 B2 | 5/2016 | Williams, Jr. et al. |
| 9,474,857 B2 | 10/2016 | Riley et al. |
| 9,480,788 B2 | 11/2016 | Wagner |
| 9,480,791 B2 | 11/2016 | Reilly |
| 9,555,379 B2 | 1/2017 | Schriver et al. |
| 9,566,381 B2 | 2/2017 | Barron et al. |
| 9,855,387 B2 | 1/2018 | Small et al. |
| 9,861,752 B2 | 1/2018 | Buder et al. |
| 9,901,671 B2 | 2/2018 | Toews et al. |
| 9,987,413 B2 | 6/2018 | Seibold et al. |
| 10,041,483 B2 | 8/2018 | Chappel et al. |
| 10,112,008 B2 | 10/2018 | Neftel et al. |
| 10,124,110 B2 | 11/2018 | Dedig et al. |
| 10,201,666 B2 | 2/2019 | Cowan et al. |
| D847,985 S | 5/2019 | Neff et al. |
| 10,391,234 B2 | 8/2019 | Sams et al. |
| 10,398,353 B2 | 9/2019 | Addison et al. |
| 10,507,319 B2 | 12/2019 | Haury et al. |
| 10,549,084 B2 | 2/2020 | Sokolov et al. |
| 10,583,256 B2 | 3/2020 | Berry et al. |
| 10,898,638 B2 | 1/2021 | Spohn et al. |
| 2001/0018937 A1 | 9/2001 | Nemoto |
| 2001/0027265 A1 | 10/2001 | Prince |

(56) References Cited

U.S. PATENT DOCUMENTS

| | | |
|---|---|---|
| 2001/0056233 A1 | 12/2001 | Uber et al. |
| 2002/0007116 A1 | 1/2002 | Zatezalo et al. |
| 2002/0010551 A1 | 1/2002 | Wang et al. |
| 2002/0099254 A1 | 7/2002 | Movahed |
| 2002/0123702 A1 | 9/2002 | Cho |
| 2002/0151854 A1 | 10/2002 | Duchon et al. |
| 2003/0050556 A1 | 3/2003 | Uber et al. |
| 2003/0120171 A1 | 6/2003 | Diamantopoulos et al. |
| 2003/0195462 A1 | 10/2003 | Mann et al. |
| 2003/0212364 A1 | 11/2003 | Mann et al. |
| 2003/0216683 A1 | 11/2003 | Shekalim |
| 2003/0226539 A1 | 12/2003 | Kim et al. |
| 2004/0011740 A1 | 1/2004 | Bernard et al. |
| 2004/0025452 A1 | 2/2004 | McLean |
| 2004/0044302 A1 | 3/2004 | Bernard et al. |
| 2004/0092905 A1 | 5/2004 | Azzolini |
| 2004/0097806 A1 | 5/2004 | Hunter et al. |
| 2004/0154788 A1 | 8/2004 | Symonds |
| 2004/0162484 A1 | 8/2004 | Nemoto |
| 2004/0163655 A1 | 8/2004 | Gelfand et al. |
| 2004/0167415 A1 | 8/2004 | Gelfand et al. |
| 2004/0171923 A1 | 9/2004 | Kalafut et al. |
| 2004/0215144 A1 | 10/2004 | Duchon et al. |
| 2004/0253183 A1 | 12/2004 | Uber, III et al. |
| 2005/0107697 A1 | 5/2005 | Berke et al. |
| 2005/0113766 A1 | 5/2005 | Mottola et al. |
| 2005/0171487 A1 | 8/2005 | Haury et al. |
| 2005/0234428 A1 | 10/2005 | Spohn et al. |
| 2006/0052794 A1 | 3/2006 | Mcgill et al. |
| 2006/0079765 A1 | 4/2006 | Neer et al. |
| 2006/0079843 A1 | 4/2006 | Brooks et al. |
| 2006/0135940 A1 | 6/2006 | Joshi |
| 2006/0167415 A1 | 7/2006 | Nemoto |
| 2006/0173360 A1 | 8/2006 | Kalafut et al. |
| 2006/0211970 A1 | 9/2006 | Sciulli |
| 2007/0068964 A1 | 3/2007 | Tanaami et al. |
| 2007/0129705 A1 | 6/2007 | Trombley et al. |
| 2007/0161970 A1 | 7/2007 | Spohn et al. |
| 2007/0219496 A1 | 9/2007 | Kamen et al. |
| 2007/0276327 A1 | 11/2007 | Kalafut et al. |
| 2008/0015406 A1 | 1/2008 | Dlugos et al. |
| 2008/0045925 A1 | 2/2008 | Stepovich et al. |
| 2008/0147147 A1 | 6/2008 | Griffiths et al. |
| 2008/0167621 A1 | 7/2008 | Wagner et al. |
| 2008/0183131 A1 | 7/2008 | Duchon et al. |
| 2009/0216192 A1 | 8/2009 | Schriver et al. |
| 2009/0234226 A1 | 9/2009 | Nemoto |
| 2009/0247865 A1 | 10/2009 | Spohn et al. |
| 2009/0247961 A1 | 10/2009 | Carlyon |
| 2009/0312744 A1 | 12/2009 | Keeley et al. |
| 2010/0113887 A1 | 5/2010 | Kalafut et al. |
| 2010/0114040 A1 | 5/2010 | Schriver et al. |
| 2010/0114064 A1 | 5/2010 | Kalafut et al. |
| 2010/0130809 A1 | 5/2010 | Morello |
| 2010/0249586 A1 | 9/2010 | Cocker et al. |
| 2010/0262078 A1 | 10/2010 | Blomquist |
| 2010/0331779 A1 | 12/2010 | Nystrom et al. |
| 2011/0275988 A1 | 11/2011 | Davis et al. |
| 2012/0089114 A1 | 4/2012 | Hemond et al. |
| 2012/0101472 A1 | 4/2012 | Schroeder et al. |
| 2012/0123229 A1 | 5/2012 | Butterfield et al. |
| 2012/0178629 A1 | 7/2012 | Hudson et al. |
| 2012/0203177 A1 | 8/2012 | Lanier, Jr. et al. |
| 2012/0204997 A1 | 8/2012 | Winn et al. |
| 2012/0217231 A1 | 8/2012 | Moore et al. |
| 2012/0229270 A1 | 9/2012 | Morley et al. |
| 2012/0245560 A1 | 9/2012 | Hochman |
| 2013/0030290 A1 | 1/2013 | Nemoto |
| 2013/0123619 A1 | 5/2013 | Griggs |
| 2013/0245439 A1 | 9/2013 | Small et al. |
| 2013/0245604 A1 | 9/2013 | Kouyoumjian et al. |
| 2013/0261993 A1 | 10/2013 | Ruchti et al. |
| 2013/0274599 A1 | 10/2013 | Bouton et al. |
| 2014/0142537 A1 | 5/2014 | Gibson et al. |
| 2014/0261713 A1* | 9/2014 | Schriver .............. B01F 27/50 366/182.2 |
| 2014/0276550 A1 | 9/2014 | Uram et al. |
| 2016/0030662 A1 | 2/2016 | Uber, III et al. |
| 2016/0224750 A1 | 8/2016 | Kethman et al. |
| 2016/0278725 A1 | 9/2016 | Van Nijnatten |
| 2016/0310085 A1 | 10/2016 | Delia |
| 2016/0331896 A1 | 11/2016 | Nemoto et al. |
| 2016/0331951 A1 | 11/2016 | Sokolov et al. |
| 2016/0346485 A1 | 12/2016 | Mohr et al. |
| 2017/0035974 A1 | 2/2017 | Berry et al. |
| 2017/0056603 A1 | 3/2017 | Cowan et al. |
| 2017/0100534 A1 | 4/2017 | Fukikoshi et al. |
| 2017/0136424 A1 | 5/2017 | Schriver et al. |
| 2017/0143898 A1 | 5/2017 | Grosse-Wentrup et al. |
| 2017/0196702 A1 | 7/2017 | Agarwal et al. |
| 2017/0232173 A1 | 8/2017 | Perry et al. |
| 2017/0258982 A1 | 9/2017 | Kemper |
| 2017/0290971 A1 | 10/2017 | Hedmann et al. |
| 2017/0312430 A1 | 11/2017 | Schleicher et al. |
| 2017/0343446 A1 | 11/2017 | Ciolkosz et al. |
| 2017/0361017 A1 | 12/2017 | Verma et al. |
| 2018/0015274 A1 | 1/2018 | Haury et al. |
| 2018/0133392 A1 | 5/2018 | Dembo et al. |
| 2018/0161496 A1 | 6/2018 | Berry et al. |
| 2018/0261496 A1 | 9/2018 | Liu et al. |
| 2018/0296755 A1 | 10/2018 | Dahlin et al. |
| 2019/0134297 A1 | 5/2019 | Kamen et al. |
| 2019/0201082 A1 | 7/2019 | Shelton, IV et al. |
| 2019/0328339 A1 | 10/2019 | Gujral et al. |
| 2020/0035355 A1 | 1/2020 | Xavier et al. |
| 2020/0129702 A1 | 4/2020 | Pedersen |
| 2020/0146647 A1 | 5/2020 | Uber, III et al. |
| 2020/0149948 A1 | 5/2020 | McDermott et al. |
| 2020/0246541 A1 | 8/2020 | Neftel et al. |
| 2021/0338922 A1 | 11/2021 | Uber, III et al. |
| 2022/0001092 A1 | 1/2022 | Benamou et al. |

FOREIGN PATENT DOCUMENTS

| | | |
|---|---|---|
| CA | 2234050 A1 | 4/1997 |
| CN | 1671428 A | 9/2005 |
| CN | 103347552 A | 10/2013 |
| DE | 3203594 A1 | 8/1983 |
| DE | 3726452 A1 | 2/1989 |
| DE | 4426387 A1 | 8/1995 |
| DE | 19702896 A1 | 7/1997 |
| DE | 19647701 A1 | 5/1998 |
| DE | 19919572 A1 | 11/2000 |
| EP | 0121216 A1 | 10/1984 |
| EP | 0129910 A1 | 1/1985 |
| EP | 0189491 A1 | 8/1986 |
| EP | 0192786 A2 | 9/1986 |
| EP | 0245160 A1 | 11/1987 |
| EP | 0319275 A1 | 6/1989 |
| EP | 0337924 A2 | 10/1989 |
| EP | 0343501 A2 | 11/1989 |
| EP | 0364966 A1 | 4/1990 |
| EP | 0365301 A1 | 4/1990 |
| EP | 0372152 A1 | 6/1990 |
| EP | 0378896 A2 | 7/1990 |
| EP | 0429191 A2 | 5/1991 |
| EP | 0471455 A2 | 2/1992 |
| EP | 0475563 A1 | 3/1992 |
| EP | 0595474 A2 | 5/1994 |
| EP | 0600448 A2 | 6/1994 |
| EP | 0619122 A1 | 10/1994 |
| EP | 0439711 B1 | 5/1995 |
| EP | 0869738 A1 | 10/1998 |
| EP | 1016427 A2 | 7/2000 |
| EP | 1769849 A1 | 4/2007 |
| EP | 1800704 A1 | 6/2007 |
| EP | 2692375 A1 | 2/2014 |
| EP | 2990073 A1 | 3/2016 |
| EP | 1838365 B1 | 2/2019 |
| FR | 2493708 A1 | 5/1982 |
| FR | 2561949 A1 | 10/1985 |
| GB | 201800 A | 8/1923 |
| GB | 2252656 A | 8/1992 |

(56) References Cited

FOREIGN PATENT DOCUMENTS

| | | |
|---|---|---|
| GB | 2328745 A | 3/1999 |
| JP | S5017781 A | 2/1975 |
| JP | S5815842 A | 1/1983 |
| JP | S59214432 A | 12/1984 |
| JP | S60194934 A | 10/1985 |
| JP | S60194935 A | 10/1985 |
| JP | S60253197 A | 12/1985 |
| JP | S62216199 A | 9/1987 |
| JP | S6340538 A | 2/1988 |
| JP | S63290547 A | 11/1988 |
| JP | H101207038 A | 8/1989 |
| JP | H02224647 A | 9/1990 |
| JP | H02234747 A | 9/1990 |
| JP | H0355040 A | 3/1991 |
| JP | H04115677 A | 4/1992 |
| JP | H10584296 A | 4/1993 |
| JP | H07178169 A | 7/1995 |
| JP | H0849598 A | 2/1996 |
| JP | H0999034 A | 4/1997 |
| JP | H10211198 A | 8/1998 |
| JP | 2000175900 A | 6/2000 |
| JP | 2003102724 A | 4/2003 |
| JP | 2003116843 A | 4/2003 |
| JP | 2003210456 A | 7/2003 |
| JP | 2003225234 A | 8/2003 |
| JP | 2004174008 A | 6/2004 |
| JP | 2004236849 A | 8/2004 |
| JP | 2004298550 A | 10/2004 |
| JP | 2011234774 A | 11/2011 |
| JP | 4960180 B2 | 6/2012 |
| JP | 5063593 B2 | 10/2012 |
| JP | 5203971 B2 | 6/2013 |
| JP | 5227791 B2 | 7/2013 |
| JP | 5485885 B2 | 5/2014 |
| JP | 5490840 B2 | 5/2014 |
| JP | 5511409 B2 | 6/2014 |
| JP | 5882595 B2 | 3/2016 |
| JP | 5897798 B2 | 3/2016 |
| JP | 6552258 B2 | 7/2019 |
| JP | 6618673 B2 | 12/2019 |
| JP | 6644469 B2 | 2/2020 |
| JP | 6676377 B2 | 4/2020 |
| JP | 6792104 B2 | 11/2020 |
| JP | 6839853 B2 | 3/2021 |
| WO | 8001754 A1 | 9/1980 |
| WO | 8500292 A1 | 1/1985 |
| WO | 8803815 A1 | 6/1988 |
| WO | 9114232 A1 | 9/1991 |
| WO | 9114233 A1 | 9/1991 |
| WO | 9315658 A1 | 8/1993 |
| WO | 9325141 A1 | 12/1993 |
| WO | 9415664 A1 | 7/1994 |
| WO | 9632975 A1 | 10/1996 |
| WO | 9712550 A1 | 4/1997 |
| WO | 9820919 A1 | 5/1998 |
| WO | 9924095 A2 | 5/1999 |
| WO | 0061216 A1 | 10/2000 |
| WO | 0141835 A2 | 6/2001 |
| WO | 03015633 A1 | 2/2003 |
| WO | 2004012787 A2 | 2/2004 |
| WO | 2004035116 A1 | 4/2004 |
| WO | 2004091688 A2 | 10/2004 |
| WO | 2005016165 A1 | 2/2005 |
| WO | 2005035995 A1 | 4/2005 |
| WO | 2006042093 A1 | 4/2006 |
| WO | 2006074415 A2 | 7/2006 |
| WO | 2007079016 A2 | 7/2007 |
| WO | 2007092618 A2 | 8/2007 |
| WO | 2007116840 A1 | 10/2007 |
| WO | 2007116862 A1 | 10/2007 |
| WO | 2007116891 A1 | 10/2007 |
| WO | 2007133942 A2 | 11/2007 |
| WO | 2008078604 A1 | 7/2008 |
| WO | 2008106108 A1 | 9/2008 |
| WO | 2008153831 A2 | 12/2008 |
| WO | 2009026420 A1 | 2/2009 |
| WO | 2009042577 A2 | 4/2009 |
| WO | 2009051995 A1 | 4/2009 |
| WO | 2010027636 A1 | 3/2010 |
| WO | 2010117841 A1 | 10/2010 |
| WO | 2011002744 A1 | 1/2011 |
| WO | 2011011346 A1 | 1/2011 |
| WO | 2011097487 A2 | 8/2011 |
| WO | 2011125303 A1 | 10/2011 |
| WO | 2012048277 A2 | 4/2012 |
| WO | 2012155035 A1 | 11/2012 |
| WO | 2013043868 A1 | 3/2013 |
| WO | 2014035672 A2 | 3/2014 |
| WO | 2014049656 A1 | 4/2014 |
| WO | 2014144651 A2 | 9/2014 |
| WO | 2014179326 A1 | 11/2014 |
| WO | 2014190264 A1 | 11/2014 |
| WO | 2015106107 A1 | 7/2015 |
| WO | 2015164783 A1 | 10/2015 |
| WO | 2016004329 A1 | 1/2016 |
| WO | 2016112163 A1 | 7/2016 |
| WO | 2016172467 A1 | 10/2016 |
| WO | 2016191485 A1 | 12/2016 |
| WO | 2017012781 A1 | 1/2017 |
| WO | 2017038575 A1 | 3/2017 |
| WO | 2017096072 A1 | 6/2017 |
| WO | 2017152036 A1 | 9/2017 |
| WO | 2018060505 A1 | 4/2018 |
| WO | 2018075379 A1 | 4/2018 |
| WO | 2018075386 A1 | 4/2018 |
| WO | 2018089882 A1 | 5/2018 |
| WO | 2020046869 A1 | 3/2020 |

OTHER PUBLICATIONS

The International Search Report and Written Opinion mailed Jul. 18, 2014 from corresponding PCT Application No. PCT/US2014/026324, which was filed on Mar. 13, 2014.

Angelini, P., "Use of mechanical injectors during percutaneous transluminal coronary angioplasty (PTCA)," Catheterization and Cardiovascular Diagnosis, vol. 16, Issue 3, pp. 193-194, Mar. 1989.

Awai, K., et al., "Effect of contrast material injection duration and rate on aortic peak time and peak enhancement at dynamic CT involving injection protocol with dose tailored to patient weight," Radiology, vol. 230, Issue 1, pp. 142-150, 2004.

Bae, et al. "Aortic and Hepatic Contrast Medium Enhancement at CT—Part I, Prediction with a Computer Model", Radiology 1998;207:647-655.

Bae, K.T., et al., "Multiphasic Injection Method for Uniform Prolonged Vascular Enhancement at CT Angiography: Pharmacokinetic Analysis and Experimental Porcine Model," Radiology, vol. 216, Issue 3, pp. 872-880 (Sep. 2000).

Bae, K.T. et al, "Peak Contrast Enhancement in CT and MR Angiography: When Does it Occur and Why? Pharmacokinetic Study in a Porcine Model", Radiology, vol. 227, Jun. 2003, pp. 809-816.

Bae, K.T., et al., "Uniform vascular contrast enhancement and reduced contrast medium vol. achieved by using exponentially decelerated contrast material injection method," Radiology, vol. 231, Issue 3, pp. 732-736, 2004.

Baker, Aaron; et al. "Fluid Mechanics Analysis of a Spring-Loaded Jet Injector." IEEE Transactions on Biomedical Engineering, vol. 46, No. 2, Feb. 1999.

Becker, C.R., et al., "Optimal contrast application for cardiac 4-detector-row computed tomography," Investigative Radiology, vol. 38, Issue 11, pp. 690-694 (Nov. 2003).

Blomley, M.J.K. and Dawson, P., "Bolus Dynamics: Theoretical and Experimental Aspects," The Brit. J. ofRadiology, vol. 70, No. 832, pp. 351-359 (Apr. 1997).

Brunette J.; et al., "Comparative rheology of low- and iso-osmolarity contrast agents at different temperature", Catheterization and Cardiovascular Interventions, 2008, vol. 71 Issue No. 1, 78-83.

Cademartiri, F. and Luccichenti, G., et al. "Sixteen-row multislice computed tomography: basic concepts, protocols, and enhanced clinical applications," Seminars in Ultrasound, CT and MRI, vol. 25, Issue 1, pp. 2-16, 2004.

(56) References Cited

OTHER PUBLICATIONS

Dardik, H. et al., "Remote Hydraulic Syringe Actuator," Arch. Surg., vol. 115, Issue 1, Jan. 1980.
Dawson, P. and Blomley, M., "The value of mathematical modelling in understanding contrast enhancement in CT with particular reference to the detection of hypovascular liver metastases," European Journal of Radiology, vol. 41, Issue 3, pp. 222-236 (Mar. 2002).
"Digital Injector for Angiography", Sias. (Sep. 7, 1993).
Disposable Low-Cost Catheter Tip Sensor Measures Blood Pressure during Surgery, Sensor (Jul. 1989).
EZ Chem Brochure, E-Z-EM, Inc. (Jul. 2007).
Fisher, M.E. and Teo, K.L., "Optimal insulin infusion resulting from a mathematical model of blood glucose dynamics", IEEE Transactions on Biomedical Engineering, vol. 36, Issue 4, pp. 479-486, 1989.
Flegal, K.M., et al., "Prevalence and trends in obesity among US adults," JAMA, 2002, vol. 288, Issue 14, pp. 1-4, (1999-2000).
Fleischmann, D. and Hittmair, K., "Mathematical analysis of arterial enhancement and optimization of bolus geometry for CT angiography using the discrete Fourier transform," Journal of Computer Assisted Tomography, vol. 23, Issue 3, pp. 474-484 (May/Jun. 1999).
Fleischmann, D., "Contrast Medium Injection Technique," In: U. Joseph Schoepf: "Multidetector-Row CT of the Thorax," pp. 47-59 (Jan. 22, 2004).
Fleischmann, D., "Present and Future Trends in Multiple Detector-Row CT Applications; CT Angiography", European Radiology, vol. 12, Issue 2, Supplement 2, Jul. 2002, pp. s11-s15.
Gardiner, G. A., et al., "Selective Coronary Angiography Using a Power Injector," AJR Am J Roentgenol., vol. 146, Issue 4, pp. 831-833 (Apr. 1986).
Garrett, J. S., et al., "Measurement of cardiac output by cine computed tomography," The American Journal of Cardiology, vol. 56, Issue 10, pp. 657-661, 1985.
Gembicki, F.W., "Vector Optimization for Control with Performance and Parameter Sensitivity Indices," PHD Thesis Case Western Reserve University, 1974.
Gentilini A., et al., "A new paradigm for the closed-loop intraoperative administration of analgesics in humans," IEEE Transactions on Biomedical Engineering, vol. 49, Issue 4, pp. 289-299 (Apr. 2002).
Gerlowski L.E. and Jain R.K., "Physiologically Based Pharmacokinetic Modeling: Principles and Applications," Journal of Pharmaceutical Sciences, vol. 72, pp. 1104-1125, Oct. 1983.
Goss, J. E., et al., "Power injection of contrast media during percutaneous transluminal coronary artery angioplasty," Catheterization and Cardiovascular Diagnosis, vol. 16, Issue 3, pp. 195-198 (Mar. 1989).
Grant, S.C.D. et al., "Reduction of Radiation Exposure to the Cardiologist during Coronary Angiography by the Use of a Remotely Controlled Mechanical Pump for Injection of Contrast Medium," Catheterization and Cardiovascular Diagnosis, vol. 25, Issue 2, pp. 107-109 (Feb. 1992).
Hackstein, N. et al., "Glomerular Filtration Rate Measured by Using Triphasic Helical CT with a Two-Point Patlak Plot Technique," Radiology, vol. 230, Issue 1, pp. 221-226, Jan. 2004.
Hansen, P.C, Regularization tools: a MATLAB package for analysis and solution of discrete ill-posed problems, Numerical Algorithms, vol. 6, Issue 1, pp. 35, 1994.
Hansen, P.C., "The truncated SVD as a method for regularization," BIT Numerical Mathematics, vol. 27, Issue 4, pp. 534-555, 1987.
Harris P., H. D. "The Human Pulmonary Circulation," Edinburgh, Churchill Livingstone, (Appendix I), 1986.
Hayes, M., "Statistical Digital Signal Processing and Modeling", New York, New York, Wiley and Sons, 1996, pp. 154-177, (Prony's method).
Heiken; J.P. et al., "Dynamic Contrast-Enhanced CT of the Liver: Comparison of Contrast Medium Injection Rates and Uniphasic and Biphasic Injection Protocols", Radiology, May 1993, vol. 187, No. 2, pp. 327-331.

"Infus O.R. Multi-Drug Syringe Pump with Smart Labels," Bard MedSystems Division Inc., pp. 2693-2696 (2005).
"International Preliminary Report on Patentability from PCT Application No. PCT/US2019/028124", Oct. 29, 2020.
Ireland, M.A., et al., "Safety and Convenience of a Mechanical Injector Pump for Coronary Angiography," Catheterization and Cardiovascular Diagnosis, vol. 16, Issue 3, pp. 199-201 (1989).
Jacobs, J.R., "Algorithm for optimal linear model-based control with application to pharmacokinetic model-driven drug delivery," IEEE Transactions on Biomedical Engineering, vol. 37, Issue 1, pp. 107-109 (Jan. 1990).
Korosec, F.R., "Physical Principles of Phase-Contrast, Time-of-Flight, and Contrast-Enhanced MR Angiography," 41st Annual Meeting of American Association of Physicists in Medicine, Jul. 25-29, 1999.
Korosec, Frank, "Basic Principles of Phase-contrast, Time-of-flight, and Contrast-enhanced MR Angiography", 1999.
Krause, W, "Application of pharmacokinetics to computed tomography: injection rates and schemes: mono-, bi-, or multiphasic?," Investigative Radiology, vol. 31, Issue 2, pp. 91-100, Feb. 1996.
Krieger, R. A., "CO2-Power-Assisted Hand-Held Syringe: Better Visualization during Diagnostic and Interventional Angiography," Cathet Cardiovasc Diagn., vol. 19, Issue 2, pp. 123-128 (Feb. 1990).
Liebel-Flarsheim Company, "Angiomat 6000 Digital Injection System—Operator's Manual", Document No. 600950, Rev. 1, Jan. 1990.
Mahnken, A. H., et al., "Determination of cardiac output with multislice spiral computed tomography: a validation study," Investigative Radiology, vol. 39, Issue 8, pp. 451-454, Aug. 2004.
Mahnken, A. H., et al., "Measurement of cardiac output from a test-bolus injection in multislice computed tomography," European Radiology, vol. 13, Issue 11, pp. 2498-2504, 2003.
Mark V/Mark V Plus Injector Operation Manual KMP 805P Rev. B. Medrad, Inc, 1990.
McClellan, J.H., "Parametric Signal Modeling," Chapter 1 in Advanced Topics in Signal Processing, Pentice-Hall, Englewood Cliffs, NJ (1988).
MCT and MCT Plus Injection Systems Operation Manual KMP 810P, Medrad, Inc, 1991.
"International Preliminary Report on Patentability from PCT Application No. PCT/US2019/048276", Mar. 11, 2021.
Angiography, Catheterization and Cardiovascular Diagnosis, vol. 19, pp. 123-128, 1990.
Awai Kazuo; et al, "Aortic and Hepatic Enhancement and Tumor-to-Liver Contrast: Analysis of the Effect of Different Concentrations of Contrast Material at Multi-Detector Row Helical CT.", Radiology, 2002, vol. 224; Issue 3., 757-763.
Brenner et al, Radiation Exposure From Medical Imaging: Time to Regulate?, JAMA, Jul. 14, 2010, vol. 304 No 2, 208-209.
Extravasation Sensor Support System LD Operation Manual, Nemoto Kyorindo Co Ltd, Sep. 13, 2012, Rev 4.
Kern et al, Multi-Sensor Activity Context Detection for Wearable Computing, 2016.
Sachiko T. Cochran et al., Trends in Adverse Events After IV Administration of Contrast Media, Am. J. of Roentgenology, Jun. 2001, 176, 1385-1388.
Shaqdan et al, Incidence of contrast medium extravastion for CT and MRI in a large academic medical centre: A report on 502,391 injections, Clinical Radiology, Elsevier, 2014, 69, 1264-1272.
"The Solution for Our IV Formulas", IV 6500 Formulator Volumetric Pump, Valley Lab Inc., 39C 9410976 0000071 s, E-39-15, pp. 3399-3400, As early as 1980.
Vinod et al., Acute compartment syndrome of hand resulting from radiograph contrast iohexol exravasation, Journal of Pharmacology and Pharmacotherapeutics, 2016, 44-7, 7-44.
McCullough, et al., "Risk Prediction of Contrast-Induced Nephropathy", The American Journal of Cardiology, Sep. 18, 2006, vol. 98.
Morden Peter.; et al, "The Role of Saline Flush Injection Rate in Displacement of CT Injectable Peripherally Inserted Central Catheter Tip During Power Injection of Contrast Material", AJR, Jan. 2014, 202, W13-W18.
Neatpisarnvanit, C. and Boston, J.R., "Estimation of plasma insulin from plasma glucose", IEEE Transactions on Biomedical Engineering, vol. 49, Issue 11, pp. 1253-1259, 2002.

(56) References Cited

OTHER PUBLICATIONS

Ostergaard, L., et al., "High resolution measurement of cerebral blood flow using intravascular tracer boluspassages. Part 1: Mathematical approach and statistical analysis," Magnetic Resonance in Medicine, vol. 36, Issue 5,pp. 715-725 (Nov. 1996).

Ostergaard, L., et al., "High resolution measurement of cerebral blood flow using intravascular tracer boluspassages. Part II: Experimental comparison and preliminary results," Magn Reson Med, vol. 36, Issue 5, pp. 726-736(Nov. 1996).

Parker, K.J., et al., "A Particulate Contrast Agent With Potential For Ultrasound Imaging of Liver," Ultrasound in Medicine & Biology, vol. 13, Issue 9, pp. 555-566 (Sep. 1987).

Rosen, B.R. et al., "Perfusion Imaging with NMR Contrast Agents," Magentic Resonance in Medicine, vol. 14, No. 2, pp. 249-265, May 1, 1990.

Sablayrolles, J-L, "Cardiac CT: Experience from Daily Practice", Advance CT, A GE Healthcare Publication. Aug. 2004.

Stevens, M.A., et al. "A Prospective Randomized Trial of Prevention Measures in Patients at High Risk for Contrast Nephropathy," J. of the ACC, vol. 33, Issue 2, pp. 403-411, Feb. 1999.

Swiss; Medical Care., "CT Expres Contrast Media Delivery System Operation Manual Rev 1", 2004.

"The Solution for Your IV Formulas", Valley Lab. Inc., E-39-15, 3399, 3400, 2646.

Ulrich; Medical., "Instructions for Use for ulrichINJECT CT motion—CT Contrast Media Injector", 2018.

Wada D.R. and Ward; D.S., "The hybrid model: a new pharmacokinetic model for computer-controlled infusion pumps", IEEE Transactions on Biomedical Engineering, 1994, vol. 41, Issue 2, pp. 134-142.

Wada, D.R. and Ward, D.S., "Open loop control of multiple drug effects in anesthesia", IEEE Transactions on Biomedical Engineering, vol. 42, Issue 7, pp. 666-677, 1995.

Yamashita, Y. et al., "Abdominal Helical CT: Evaluation of Optimal Doses of Intravenous Contrast Material—A Prospective Randomized Study," Radiology, vol. 216, Issue 3, pp. 718-723, Sep. 1, 2000.

Singh et al. 2008 J. Nucl. Med. Technol. 36:69274 (Year: 2008).

\* cited by examiner

FLUID INJECTOR SYSTEM WITH IMPROVED RATIO PERFORMANCE

CROSS-REFERENCE TO RELATED APPLICATION

This application is a U.S. national phase application under 35 U.S.C. § 371 of PCT International Application No. PCT/US2019/048276, filed Aug. 27, 2019 and claims the benefit of U.S. Provisional Patent Application No. 62/723,724, filed Aug. 28, 2018, the disclosures of which are hereby incorporated by reference in their entirety.

BACKGROUND OF THE DISCLOSURE

Field of the Disclosure

The present disclosure is related to a fluid injector system and, particularly, to a fluid injector system configured to perform a multi-phase injection protocol. The present disclosure is further related to a fluid injector system having improved ratio performance of a first fluid and a second fluid during a multi-phase injection protocol. The present disclosure is further directed to a method of improving ratio performance of a first fluid and a second fluid during a multi-phase injection protocol using a fluid injector system. The present disclosure is also directed to a computer program product for improving ratio performance of a first and a second fluid during a multi-phase injection protocol using a fluid injector system.

Description of Related Art

In many medical diagnostic and therapeutic procedures, a medical practitioner, such as a physician or radiologist, injects a patient with one or more fluids. In recent years, a number of injector-actuated syringes and powered injectors for pressurized injection of fluids have been developed for use in procedures such as angiography, computed tomography (CT), molecular imaging (such as PET imaging), and magnetic resonance imaging (MRI). In these procedures, a fluid, such as a contrast agent, may be used to highlight certain internal organs or portions of the body during an imaging process. Meanwhile, saline, or a similar flushing agent, may be used to ensure complete injection of the bolus of the contrast agent or adjust the concentration of the contrast agent.

For fluid injector systems with multi-reservoir disposables set up to deliver more than one fluid type, improving ratio performance of a first fluid and a second fluid during a multi-phase injection protocol is desired. Unintended deviations from desired ratio of a first fluid to second fluid during a simultaneous delivery of both fluids may result in overly concentrated or diluted doses producing images that are non-diagnostic or of reduced quality. Accordingly, there is room for improvement in fluid injector systems, methods of improving ratio performance of a first fluid and a second fluid during a multi-phase injection protocol, and computer program products for use in the same.

SUMMARY OF THE DISCLOSURE

Accordingly, provided is a fluid injector system configured to perform a multi-phase injection protocol. Also provided is a fluid injector system having improved ratio performance of a first fluid and a second fluid during a multi-phase injection protocol. Also provided is a method of improving ratio performance of a first fluid and a second fluid during a multi-phase injection protocol using a fluid injector system. Also provided is a computer program product for improving ratio performance of a first fluid and a second fluid during a multi-phase injection protocol using a fluid injector system.

In some examples or aspects of the present disclosure, a fluid injector system may be configured to perform an injection protocol including at least a first phase and a second phase, with the second phase being subsequent to the first phase. The fluid injector system may include a control device operatively associated with a first drive component and a second drive component. The first drive component may be configured to pressurize and inject a first fluid from a first fluid reservoir through a fluid conduit. The second drive component may be configured to pressurize and inject a second fluid from a second fluid reservoir through the fluid conduit. The control device may include at least one processor programmed or configured to: during the first phase of the injection protocol, actuate at least the first drive component to inject the first phase through the fluid conduit. The at least one processor may be further programmed or configured to, during the first phase of the injection protocol prior to transitioning to the second phase of the injection protocol, actuate the second drive component to pressurize the second fluid relative to a pressure of the first fluid in the fluid conduit. The at least one processor may be further programmed or configured to, during the second phase of the injection protocol, actuate the second drive component to inject at least the second fluid through the fluid conduit so that a desired steady-state ratio of the first fluid and the second fluid in the second phase is reached.

In some examples or aspects of the present disclosure, the first fluid may include a contrast medium and the second fluid may include a diluent. The desired steady-state ratio of the first fluid and the second fluid in the second phase may be reached at a quicker rate than if the second drive component is not actuated prior to transitioning to the second phase of the injection protocol.

In some examples or aspects of the present disclosure, the at least one processor may be further programmed or configured to, during the first phase of the injection protocol prior to transitioning to the second phase of the injection protocol, cease actuation or reduce a speed of the first drive component. The at least one processor may be further programmed or configured to, during the second phase of the injection protocol, adjust a speed of the first drive component to inject the first fluid at a flow rate to reach the desired steady-state ratio of the first fluid and the second fluid through the fluid conduit.

In some examples or aspects of the present disclosure, the fluid injector system further may include at least a first valve controlling fluid communication between the first reservoir and the fluid conduit and a second valve controlling fluid communication between the second reservoir and the fluid conduit. The at least one processor may be further programmed or configured to close the second valve prior to pressurizing the second fluid relative to the pressure of the first fluid in the fluid conduit. The at least one processor may be further programmed or configured to: open the second valve isolating the second fluid reservoir from the first fluid reservoir and the fluid conduit during a transition from the first phase of the injection protocol to the second phase of the injection protocol.

In some examples or aspects of the present disclosure, pressurizing the second fluid relative to the pressure of the first fluid may include selecting a pressure ratio of the pressure of the first fluid and a pressure of the second fluid to reach the desired steady-state flow ratio of the first fluid and the second fluid for the second phase. Pressurizing the second fluid relative to the pressure of the first fluid may include gradually increasing a pressure of the second fluid such that, at a transition from the first phase of the injection protocol to the second phase of the injection protocol, the pressure of the second fluid is substantially equal to the pressure of the first fluid. Pressurizing the second fluid relative to the pressure of the first fluid may include gradually increasing a pressure of the second fluid such that, at a transition from the first phase of the injection protocol to the second phase of the injection protocol, the pressure of the second fluid is 20% to 150% of the pressure of the first fluid.

In some examples or aspects of the present disclosure, the at least one processor may be further programmed or configured to, during the first phase of the injection protocol prior to transitioning to the second phase of the protocol, adjusting at least one property of the injection protocol to prevent backflow of the first fluid into the second fluid reservoir. Adjusting at least one property of the injection protocol may include at least one of advancing the second drive component at a constant speed, linearly increasing a speed of the second drive component, and exponentially increasing a speed of the second drive component.

In some examples or aspects of the present disclosure, a fluid injector system may include a control device operatively associated with a first drive component and a second drive component, with the first drive component being configured to pressurize and inject a first fluid from a first fluid reservoir through a fluid conduit, and the second drive component being configured to pressurize and inject a second fluid from a second fluid reservoir through the fluid conduit. The control device may include at least one processor programmed or configured to, during the first phase of the injection protocol, actuate at least one of the first drive component and the second drive component to inject at least one of the first fluid and the second fluid through the fluid conduit at a first desired steady-state ratio. The at least one processor may be further programmed or configured to, during an initial portion of the second phase of the injection protocol, actuate the first drive component and the second drive component to inject the first fluid and the second fluid through the fluid conduit such that a volumetric ratio of the second fluid displaced from the second fluid reservoir relative to the first fluid displaced from the first fluid reservoir exceeds a second desired steady-state ratio. The at least one processor may be further programmed or configured to, subsequent to the initial portion of the second phase, actuate at least one of the first drive component and the second drive component to reduce the volumetric ratio until the volumetric ratio reaches the second desired steady-state ratio of the first fluid and the second fluid in the second phase.

In some examples or aspects of the present disclosure, the first fluid may include a contrast medium and the second fluid may include a diluent. The second desired steady-state ratio of the first fluid and the second fluid in the second phase may be reached at a quicker rate than if the actuation of the first drive component and the second drive component to inject the first fluid and the second fluid through the fluid conduit such that a volumetric ratio of the second fluid displaced from the second fluid reservoir relative to the first fluid displaced from the first fluid reservoir does not exceed a second desired steady-state ratio.

In some examples or aspects of the present disclosure, the at least one processor may be further programmed or configured to, during the first phase of the injection protocol prior to transitioning to the second phase of the injection protocol, cease actuation or reduce a speed of the first drive component.

In some examples or aspects of the present disclosure, the fluid injector system further may include at least a first valve controlling fluid communication between the first reservoir and the fluid conduit and a second valve controlling fluid communication between the second reservoir and the fluid conduit. The at least one processor may be further programmed or configured to open the second valve isolating the second fluid reservoir from the first fluid reservoir and the fluid conduit during a transition from the first phase of the injection protocol to the second phase of the injection protocol. The at least one processor may be further programmed or configured to, during the first phase of the injection protocol prior to transitioning to the second phase of the injection protocol, actuate the second drive component to pressurize the second fluid relative to a pressure of the first fluid in the fluid conduit.

In some examples or aspects of the present disclosure, the fluid injector system further may include at least a first valve controlling fluid communication between the first reservoir and the fluid conduit and a second valve controlling fluid communication between the second reservoir and the fluid conduit. The at least one processor may be further programmed or configured to close the second valve prior to pressurizing the second fluid relative to the pressure of the first fluid in the fluid conduit.

In some examples or aspects of the present disclosure, during the first phase of the injection protocol prior to transitioning to the second phase of the injection protocol, at least one processor may be further programmed or configured for adjusting at least one property of the injection protocol to prevent backflow of the first fluid into the second fluid reservoir. Adjusting at least one property of the injection protocol may include at least one of: advancing the second drive component at a constant speed, linearly increasing a speed of the second drive component, and exponentially increasing the speed of the second drive component.

In some examples or aspects of the present disclosure, a computer program product for performing an injection protocol using a fluid injector system may be provided. The computer program product may have non-transitory computer readable media including one or more instructions that, when executed by at least one processor of the fluid injector system, may cause the at least one processor to: during the first phase of the injection protocol, actuate at least a first drive component of the fluid injector system to inject the first phase including a first fluid through a fluid conduit; during the first phase of the injection protocol prior to transitioning to the second phase of the injection protocol, actuate a second drive component of the fluid injector system to pressurize a second fluid relative to a pressure of a first fluid in the fluid conduit; and during the second phase of the injection protocol, actuate the second drive component to inject at least the second fluid through the fluid conduit so that a desired steady-state ratio of the first fluid and the second fluid in the second phase is reached.

In some examples or aspects of the present disclosure, the first fluid may include a contrast medium and the second fluid may include a diluent. The desired steady-state ratio of the first fluid and the second fluid in the second phase may be reached at a quicker rate than if the second drive component is not actuated prior to transitioning to the second phase of the injection protocol.

In some examples or aspects of the present disclosure, the one or more instructions, when executed by the at least one processor of the fluid injector system, further may cause the at least one processor to: during the first phase of the injection protocol prior to transitioning to the second phase of the injection protocol, cease actuation or reduce a speed of the first drive component. The one or more instructions, when executed by at least one processor of the fluid injector system, further may cause the at least one processor to: during the second phase of the injection protocol, adjust a speed of the first drive component to inject the first fluid at a flow rate to reach the desired steady-state ratio of the first fluid and the second fluid through the fluid conduit during the second phase of the injection protocol.

In some examples or aspects of the present disclosure, the fluid injector system further may include at least a first valve controlling fluid communication between the fluid conduit and a first reservoir containing the first fluid, and a second valve controlling fluid communication between the second reservoir and the fluid conduit, and the one or more instructions, when executed by at least one processor of the fluid injector system, further may cause the at least one processor to close the second valve prior to pressurizing the second fluid relative to the pressure of the first fluid in the fluid conduit. The one or more instructions, when executed by at least one processor of the fluid injector system, further may cause the at least one processor to: open the second valve isolating the second fluid reservoir from the first fluid reservoir and the fluid conduit during a transition from the first phase of the injection protocol to the second phase of the injection protocol.

In some examples or aspects of the present disclosure, pressurizing the second fluid relative to the pressure of the first fluid may include selecting a pressure ratio of the pressure of the first fluid and a pressure of the second fluid to reach the desired steady-state flow ratio of the first fluid and the second fluid for the second phase. Pressurizing the second fluid relative to the pressure of the first fluid may include gradually increasing a pressure of the second fluid such that, at a transition from the first phase of the injection protocol to the second phase of the injection protocol, the pressure of the second fluid is substantially equal to the pressure of the first fluid. Pressurizing the second fluid relative to the pressure of the first fluid may include gradually increasing a pressure of the second fluid such that, at a transition from the first phase of the injection protocol to the second phase of the injection protocol, the pressure of the second fluid is 20% to 150% of the pressure of the first fluid.

In some examples or aspects of the present disclosure, the one or more instructions may be further programmed or configured to: during the first phase of the injection protocol prior to transitioning to the second phase of the injection protocol, adjusting at least one property of the injection protocol to prevent backflow of the first fluid into the second fluid reservoir. Adjusting at least one property of the injection protocol may include at least one of: advancing the second drive component at a constant speed, linearly increasing a speed of the second drive component, and exponentially increasing the speed of the second drive component.

In some examples or aspects of the present disclosure, a computer program product may be configured to perform an injection protocol using a fluid injector system. The injection protocol may include at least a first phase and a second phase subsequent to the first phase. The computer program product may include non-transitory computer readable media including one or more instructions that, when executed by at least one processor of the fluid injector system, may cause the at least one processor to: during the first phase of the injection protocol, actuate at least one of a first drive component, configured to pressurize and inject a first fluid from a first fluid reservoir through a fluid conduit and a second drive component, configured to pressurize and inject a second fluid from a second fluid reservoir through the fluid conduit, to inject at least one of the first fluid and the second fluid through the fluid conduit at a first desired steady-state ratio; during an initial portion of the second phase of the injection protocol, actuate the first drive component and the second drive component to inject the first fluid and the second fluid through the fluid conduit such that a volumetric ratio of the second fluid displaced from the second fluid reservoir relative to the first fluid displaced from the first fluid reservoir exceeds a second desired steady-state ratio; and subsequent to the initial portion of the second phase, actuate at least one of the first drive component and the second drive component to reduce the volumetric ratio until the volumetric ratio reaches the second desired steady-state ratio of the first fluid and the second fluid in the second phase.

In some examples or aspects of the present disclosure, the first fluid may include a contrast medium and the second fluid may include a diluent. The second desired steady-state ratio of the first fluid and the second fluid in the second phase may be reached at a quicker rate than if the actuation of the first drive component and the second drive component to inject the first fluid and the second fluid through the fluid conduit such that a volumetric ratio of the second fluid displaced from the second fluid reservoir relative to the first fluid displaced from the first fluid reservoir does not exceed a second desired steady-state ratio.

In some examples or aspects of the present disclosure, the one or more instructions, when executed by at least one processor of the fluid injector system, further may cause the at least one processor to: during the first phase of the injection protocol prior to transitioning to the second phase of the injection protocol, cease actuation or reduce a speed of the first drive component.

In some examples or aspects of the present disclosure, the fluid injector system further may include at least a first valve controlling fluid communication between the first reservoir and the fluid conduit and a second valve controlling fluid communication between the second reservoir and the fluid conduit, and the one or more instructions, when executed by at least one processor of the fluid injector system, further may cause the at least one processor to: open the second valve isolating the second drive component from the first fluid reservoir and the fluid conduit during a transition from the first phase of the injection protocol to the second phase of the injection protocol. The one or more instructions, when executed by at least one processor of the fluid injector system, further may cause the at least one processor to: during the first phase of the injection protocol prior to transitioning to the second phase of the injection protocol, actuate the second drive component to pressurize the second fluid relative to a pressure of the first fluid in the fluid conduit.

In some examples or aspects of the present disclosure, the fluid injector system further may include at least a first valve controlling fluid communication between the first reservoir and the fluid conduit and a second valve controlling fluid communication between the second reservoir and the fluid conduit, and the one or more instructions, when executed by at least one processor of the fluid injector system, further may cause the at least one processor to close the second valve prior to pressurizing the second fluid relative to the pressure of the first fluid in the fluid conduit.

In some examples or aspects of the present disclosure, the one or more instructions, when executed by at least one processor of the fluid injector system, further may cause the at least one processor to, during the first phase of the injection protocol prior to transitioning to the second phase of the injection protocol, adjust at least one property of the injection protocol to prevent backflow of the first fluid into the second fluid reservoir. Adjusting at least one property of the injection protocol may include at least one of: advancing the second drive component at a constant speed, linearly increasing a speed of the second drive component, and exponentially increasing the speed of the second drive component.

In some examples or aspects of the present disclosure, a method of performing an injection protocol including at least a first phase and a second phase using a fluid injector system may include: providing a control device operatively associated with a first drive component and a second drive component, the first drive component configured to pressurize and inject a first fluid from a first fluid reservoir through a fluid conduit, the second drive component configured to pressurize and inject a second fluid from a second fluid reservoir through the fluid conduit, actuating at least the first drive component to inject the first phase through the fluid conduit during the first phase of the injection protocol; actuating the second drive component to pressurize the second fluid relative to a pressure of the first fluid in the fluid conduit during the first phase of the injection protocol prior to transitioning to the second phase of the injection protocol; and actuating the second drive component to inject at least the second fluid through the fluid conduit so that a desired steady-state ratio of the first fluid and the second fluid in the second phase is reached during the second phase of the injection protocol.

In some examples or aspects of the present disclosure, the first fluid may include a contrast medium and the second fluid may include a diluent. The desired steady-state ratio of the first fluid and the second fluid in the second phase may be reached at a quicker rate than if the second drive component is not actuated prior to transitioning to the second phase of the injection protocol.

In some examples or aspects of the present disclosure, the method further may include ceasing actuation or reducing a speed of the first drive component during the first phase of the injection protocol prior to transitioning to the second phase of the injection protocol. The method further may include adjusting a speed of the first drive component to inject the first fluid at a flow rate to reach the desired steady-state ratio of the first fluid and the second fluid through the fluid conduit during the second phase of the injection protocol.

In some examples or aspects of the present disclosure, the fluid injector system may further include at least a first valve controlling fluid communication between the first reservoir and the fluid conduit and a second valve controlling fluid communication between the second reservoir and the fluid conduit, and the method further may include closing the second valve prior to pressurizing the second fluid relative to the pressure of the first fluid in the fluid conduit. The method further may include opening the second valve isolating the second fluid reservoir from the first fluid reservoir and the fluid conduit during a transition from the first phase of the injection protocol to the second phase of the injection protocol.

In some examples or aspects of the present disclosure, pressurizing the second fluid relative to the pressure of the first fluid may include selecting a pressure ratio of the pressure of the first fluid and a pressure of the second fluid to reach the desired steady-state flow ratio of the first fluid and the second fluid for the second phase. Pressurizing the second fluid relative to the pressure of the first fluid may include gradually increasing a pressure of the second fluid such that, at a transition from the first phase of the injection protocol to the second phase of the injection protocol, the pressure of the second fluid is substantially equal to the pressure of the first fluid. Pressurizing the second fluid relative to the pressure of the first fluid may include gradually increasing a pressure of the second fluid such that, at a transition from the first phase of the injection protocol to the second phase of the injection protocol, the pressure of the second fluid is 20% to 150% of the pressure of the first fluid.

In some examples or aspects of the present disclosure, the method further may include adjusting at least one property of the injection protocol to prevent backflow of the first fluid into the second fluid reservoir during the first phase of the injection protocol prior to transitioning to the second phase of the injection protocol. Adjusting at least one property of the injection protocol may include at least one of: advancing the second drive component at a constant speed, linearly increasing a speed of the second drive component, and exponentially increasing the speed of the second drive component.

In some examples or aspects of the present disclosure, a method of performing an injection protocol including at least a first phase and a second phase using a fluid injector system may include: providing a control device operatively associated with a first drive component and a second drive component, the first drive component configured to pressurize and inject a first fluid from a first fluid reservoir through a fluid conduit, the second drive component configured to pressurize and inject a second fluid from a second fluid reservoir through the fluid conduit, actuating at least one of the first drive component and the second drive component to inject at least one of the first fluid and the second fluid through the fluid conduit at a first desired steady-state ratio during the first phase of the injection protocol; actuating the first drive component and the second drive component to inject the first fluid and the second fluid through the fluid conduit such that a volumetric ratio of the second fluid displaced from the second fluid reservoir relative to the first fluid displaced from the first fluid reservoir exceeds a second desired steady-state ratio during an initial portion of the second phase of the injection protocol; and actuating at least one of the first drive component and the second drive component to reduce the volumetric ratio until the volumetric ratio reaches the second desired steady-state ratio of the first fluid and the second fluid in the second phase subsequent to the initial portion of the second phase.

In some examples or aspects of the present disclosure, the first fluid may include a contrast medium and the second fluid may include a diluent. The second desired steady-state ratio of the first fluid and the second fluid in the second phase may be reached at a quicker rate than if the actuation of the first drive component and the second drive component to inject the first fluid and the second fluid through the fluid conduit such that a volumetric ratio of the second fluid displaced from the second fluid reservoir relative to the first fluid displaced from the first fluid reservoir does not exceed a second desired steady-state ratio.

In some examples or aspects of the present disclosure, the method further may include ceasing actuation or reduce a speed of the first drive component during the first phase of the injection protocol prior to transitioning to the second phase of the injection protocol. The fluid injector system further may include at least a first valve controlling fluid communication between the first reservoir and the fluid conduit and a second valve controlling fluid communication between the second reservoir and the fluid conduit, and the method further may include opening the second valve isolating the second drive component from the first fluid reservoir and the fluid conduit during a transition from the first phase of the injection protocol to the second phase of the injection protocol.

In some examples or aspects of the present disclosure, the method further may include actuating the second drive component to pressurize the second fluid relative to a pressure of the first fluid in the fluid conduit during the first phase of the injection protocol prior to transitioning to the second phase of the injection protocol. The fluid injector system further may include at least a first valve controlling fluid communication between the first reservoir and the fluid conduit and a second valve controlling fluid communication between the second reservoir and the fluid conduit, and the method further may include closing the second valve prior to pressurizing the second fluid relative to the pressure of the first fluid in the fluid conduit.

In some examples or aspects of the present disclosure, the method further may include adjusting at least one property of the injection protocol to prevent backflow of the first fluid into the second fluid reservoir during the first phase of the injection protocol prior to transitioning to the second phase of the injection protocol. Adjusting at least one property of the injection protocol may include at least one of: advancing the second drive component at a constant speed, linearly increasing a speed of the second drive component, and exponentially increasing the speed of the second drive component.

Various other aspects of the present disclosure are recited in one or more of the following numbered clauses:

Clause 1: A fluid injector system configured to perform an injection protocol comprising at least a first phase and a second phase, the second phase subsequent to the first phase, the fluid injector system comprising: a control device operatively associated with a first drive component and a second drive component, the first drive component configured to pressurize and inject a first fluid from a first fluid reservoir through a fluid conduit, the second drive component configured to pressurize and inject a second fluid from a second fluid reservoir through the fluid conduit, wherein the control device comprises at least one processor programmed or configured to: during the first phase of the injection protocol, actuate at least the first drive component to inject the first phase through the fluid conduit; during the first phase of the injection protocol prior to transitioning to the second phase of the injection protocol, actuate the second drive component to pressurize the second fluid relative to a pressure of the first fluid in the fluid conduit; and during the second phase of the injection protocol, actuate the second drive component to inject at least the second fluid through the fluid conduit so that a desired steady-state ratio of the first fluid and the second fluid in the second phase is reached.

Clause 2: The fluid injector system of clause 1, wherein the first fluid comprises a contrast medium and the second fluid comprises a diluent.

Clause 3: The fluid injector system of clause 1 or 2, wherein the desired steady-state ratio of the first fluid and the second fluid in the second phase is reached at a quicker rate than if the second drive component is not actuated prior to transitioning to the second phase of the injection protocol.

Clause 4: The fluid injector system of any of clauses 1 to 3, wherein the at least one processor is further programmed or configured to: during the first phase of the injection protocol prior to transitioning to the second phase of the injection protocol, cease actuation or reduce a speed of the first drive component.

Clause 5: The fluid injector system of any of clauses 1 to 4, wherein the at least one processor is further programmed or configured to: during the second phase of the injection protocol, adjust a speed of the first drive component to inject the first fluid at a flow rate to reach a desired steady-state ratio of the first and second fluid through the fluid conduit.

Clause 6: The fluid injector system of any of clauses 1 to 5, further comprising at least a first valve controlling fluid communication between the first reservoir and the fluid conduit and a second valve controlling fluid communication between the second reservoir and the fluid conduit, wherein the at least one processor is further programmed or configured to close the second valve prior to pressurizing the second fluid relative to the pressure of the first fluid in the fluid conduit.

Clause 7: The fluid injector system of any of clauses 1 to 6, wherein the at least one processor is further programmed or configured to: open the second valve isolating the second fluid reservoir from the first fluid reservoir and the fluid conduit during a transition from the first phase of the injection protocol to the second phase of the injection protocol.

Clause 8: The fluid injector system of any of clauses 1 to 7, wherein pressurizing the second fluid relative to the pressure of the first fluid comprises selecting a pressure ratio of the pressure of the first fluid and a pressure of the second fluid to reach the desired steady-state flow ratio of the first fluid and the second fluid for the second phase.

Clause 9: The fluid injector system of any of clauses 1 to 8, wherein pressurizing the second fluid relative to the pressure of the first fluid comprises gradually increasing a pressure of the second fluid such that at a transition from the first phase of the injection protocol to the second phase of the injection protocol, the pressure of the second fluid is substantially equal to the pressure of the first fluid. The fluid injector system of any of clauses 1 to 8, wherein pressurizing the second fluid relative to the pressure of the first fluid comprises gradually increasing a pressure of the second fluid such that at a transition from the first phase of the injection protocol to the second phase of the injection protocol, the pressure of the second fluid is 20% to 150% of the pressure of the first fluid.

Clause 10: The fluid injector system of any of clauses 1 to 9, wherein the at least one processor is further programmed or configured to: during the first phase of the injection protocol prior to transitioning to the second phase of the injection protocol, adjusting at least one property of the injection protocol to prevent backflow of the first fluid into the second fluid reservoir.

Clause 11: The fluid injector system of any of clauses 1 to 10, wherein adjusting at least one property of the injection protocol comprises at least one of: advancing the second drive component at a constant speed, linearly increasing a speed of the second drive component, and exponentially increasing the speed of the second drive component.

Clause 12: A fluid injector system configured to perform an injection protocol comprising at least a first phase and a second phase, the second phase subsequent to the first phase, the fluid injector system comprising: a control device operatively associated with a first drive component and a second drive component, the first drive component configured to pressurize and inject a first fluid from a first fluid reservoir through a fluid conduit, the second drive component configured to pressurize and inject a second fluid from a second fluid reservoir through the fluid conduit, wherein the control device comprises at least one processor programmed or configured to: during the first phase of the injection protocol, actuate at least one of the first drive component and the second drive component to inject at least one of the first fluid and the second fluid through the fluid conduit at a first desired steady-state ratio; during an initial portion of the second phase of the injection protocol, actuate the first drive component and the second drive component to inject the first fluid and the second fluid through the fluid conduit such that a volumetric ratio of the second fluid displaced from the second fluid reservoir relative to the first fluid displaced from the first fluid reservoir exceeds a second desired steady-state ratio; and subsequent to the initial portion of the second phase, actuate at least one of the first drive component and the second drive component to reduce the volumetric ratio until the volumetric ratio reaches the second desired steady-state ratio of the first fluid and the second fluid in the second phase.

Clause 13: The fluid injector system of clause 12, wherein the first fluid comprises a contrast medium and the second fluid comprises a diluent.

Clause 14: The fluid injector system of clause 12 or 13, wherein the second desired steady-state ratio of the first fluid and the second fluid in the second phase is reached at a quicker rate than if the actuation of the first drive component and the second drive component to inject the first and second fluid through the fluid conduit such that a volumetric ratio of the second fluid displaced from the second fluid reservoir relative to the first fluid displaced from the first fluid reservoir does not exceed a second desired steady-state ratio.

Clause 15: The fluid injector system of any of clauses 12 to 14, wherein the at least one processor is further programmed or configured to: during the first phase of the injection protocol prior to transitioning to the second phase of the injection protocol, cease actuation or reduce a speed of the first drive component.

Clause 16: The fluid injector system of any of clauses 12 to 15, further comprising at least a first valve controlling fluid communication between the first reservoir and the fluid conduit and a second valve controlling fluid communication between the second reservoir and the fluid conduit, wherein the at least one processor is further programmed or configured to: open the second valve isolating the second drive component from the first fluid reservoir and the fluid conduit during a transition from the first phase of the injection protocol to the second phase of the injection protocol.

Clause 17: The fluid injector system of any of clauses 12 to 16, wherein the at least one processor is further programmed or configured to: during the first phase of the injection protocol prior to transitioning to the second phase of the injection protocol, actuate the second drive component to pressurize the second fluid relative to a pressure of the first fluid in the fluid conduit.

Clause 18: The fluid injector system of any of clauses 12 to 17, further comprising at least a first valve controlling fluid communication between the first reservoir and the fluid conduit and a second valve controlling fluid communication between the second reservoir and the fluid conduit, wherein the at least one processor is further programmed or configured to close the second valve prior to pressurizing the second fluid relative to the pressure of the first fluid in the fluid conduit.

Clause 19: The fluid injector system of any of clauses 12 to 18, wherein the at least one processor is further programmed or configured to: during the first phase of the injection protocol prior to transitioning to the second phase of the injection protocol, adjust at least one property of the injection protocol to prevent backflow of the first fluid into the second fluid reservoir.

Clause 20: The fluid injector system of any of clauses 12 to 19, wherein adjusting at least one property of the injection protocol comprises at least one of: advancing the second drive component at a constant speed, linearly increasing a speed of the second drive component, and exponentially increasing the speed of the second drive component.

Clause 21: A computer program product for performing an injection protocol using a fluid injector system, the injection protocol including at least a first phase and a second phase subsequent to the first phase, the computer program product comprising: non-transitory computer readable media comprising one or more instructions that, when executed by at least one processor of the fluid injector system, cause the at least one processor to: during the first phase of the injection protocol, actuate at least a first drive component of the fluid injector system to inject the first phase including a first fluid through a fluid conduit; during the first phase of the injection protocol prior to transitioning to the second phase of the injection protocol, actuate a second drive component of the fluid injector system to pressurize a second fluid relative to a pressure of a first fluid in the fluid conduit; and during the second phase of the injection protocol, actuate the second drive component to inject at least the second fluid through the fluid conduit so that a desired steady-state ratio of the first fluid and the second fluid in the second phase is reached.

Clause 22: The computer program product of clause 21, wherein the first fluid comprises a contrast medium and the second fluid comprises a diluent.

Clause 23: The computer program product of clause 21 or 22, wherein the desired steady-state ratio of the first fluid and the second fluid in the second phase is reached at a quicker rate than if the second drive component is not actuated prior to transitioning to the second phase of the injection protocol.

Clause 24: The computer program product of any of clauses 21 to 23, wherein the one or more instructions, when executed by the at least one processor of the fluid injector system, further cause the at least one processor to: during the first phase of the injection protocol prior to transitioning to the second phase of the injection protocol, cease actuation or reduce a speed of the first drive component.

Clause 25: The computer program product of any of clauses 21 to 24, wherein the one or more instructions, when executed by at least one processor of the fluid injector system, further cause the at least one processor to: during the second phase of the injection protocol, adjust a speed of the first drive component to inject the first fluid at a flow rate to reach the desired steady-state ratio of the first fluid and the second fluid through the fluid conduit during the second phase of the injection protocol.

Clause 26: The computer program product of any of clauses 21 to 25, wherein the fluid injector system further comprises at least a first valve controlling fluid communication between the fluid conduit and a first reservoir containing the first fluid, and a second valve controlling fluid communication between the second reservoir and the fluid conduit, and wherein the one or more instructions, when executed by at least one processor of the fluid injector system, further cause the at least one processor to close the second valve prior to pressurizing the second fluid relative to the pressure of the first fluid in the fluid conduit.

Clause 27: The computer program product of clause 26, wherein the one or more instructions, when executed by at least one processor of the fluid injector system, further cause the at least one processor to: open the second valve isolating the second fluid reservoir from the first fluid reservoir and the fluid conduit during a transition from the first phase of the injection protocol to the second phase of the injection protocol.

Clause 28: The computer program product of any of clauses 21 to 27, wherein pressurizing the second fluid relative to the pressure of the first fluid comprises selecting a pressure ratio of the pressure of the first fluid and a pressure of the second fluid to reach the desired steady-state flow ratio of the first fluid and the second fluid for the second phase.

Clause 29: The computer program product of any of clauses 21 to 28, wherein pressurizing the second fluid relative to the pressure of the first fluid comprises gradually increasing a pressure of the second fluid such that, at a transition from the first phase of the injection protocol to the second phase of the injection protocol, the pressure of the second fluid is substantially equal to the pressure of the first fluid. The computer program product of any of clauses 21 to 28, wherein pressurizing the second fluid relative to the pressure of the first fluid comprises gradually increasing a pressure of the second fluid such that at a transition from the first phase of the injection protocol to the second phase of the injection protocol, the pressure of the second fluid is 20% to 150% of the pressure of the first fluid.

Clause 30: The computer program product of any of clauses 21 to 29, wherein the at least one processor is further programmed or configured to: during the first phase of the injection protocol prior to transitioning to the second phase of the injection protocol, adjusting at least one property of the injection protocol to prevent backflow of the first fluid into the second fluid reservoir.

Clause 31: The computer program product of clause 30, wherein adjusting at least one property of the injection protocol comprises at least one of: advancing the second drive component at a constant speed, linearly increasing a speed of the second drive component, and exponentially increasing the speed of the second drive component.

Clause 32: A computer program product configured to perform an injection protocol using a fluid injector system, the injection protocol including at least a first phase and a second phase subsequent to the first phase, the computer program product comprising: non-transitory computer readable media comprising one or more instructions that, when executed by at least one processor of the fluid injector system, cause the at least one processor to: during the first phase of the injection protocol, actuate at least one of a first drive component, configured to pressurize and inject a first fluid from a first fluid reservoir through a fluid conduit and a second drive component, configured to pressurize and inject a second fluid from a second fluid reservoir through the fluid conduit, to inject at least one of the first fluid and the second fluid through the fluid conduit at a first desired steady-state ratio; during an initial portion of the second phase of the injection protocol, actuate the first drive component and the second drive component to inject the first fluid and the second fluid through the fluid conduit such that a volumetric ratio of the second fluid displaced from the second fluid reservoir relative to the first fluid displaced from the first fluid reservoir exceeds a second desired steady-state ratio; and subsequent to the initial portion of the second phase, actuate at least one of the first drive component and the second drive component to reduce the volumetric ratio until the volumetric ratio reaches the second desired steady-state ratio of the first fluid and the second fluid in the second phase.

Clause 33: The computer program product of clause 32, wherein the first fluid comprises a contrast medium and the second fluid comprises a diluent.

Clause 34: The computer program product of clause 32 or 33, wherein the second desired steady-state ratio of the first fluid and the second fluid in the second phase is reached at a quicker rate than if the actuation of the first drive component and the second drive component to inject the first fluid and the second fluid through the fluid conduit such that a volumetric ratio of the second fluid displaced from the second fluid reservoir relative to the first fluid displaced from the first fluid reservoir does not exceeds a second desired steady-state ratio.

Clause 35: The computer program product of any of clauses 32 to 34, wherein the one or more instructions, when executed by at least one processor of the fluid injector system, further cause the at least one processor to: during the first phase of the injection protocol prior to transitioning to the second phase of the injection protocol, cease actuation or reduce a speed of the first drive component.

Clause 36: The computer program product of any of clauses 32 to 35, wherein the fluid injector system further comprises at least a first valve controlling fluid communication between the first reservoir and the fluid conduit and a second valve controlling fluid communication between the second reservoir and the fluid conduit, and wherein the one or more instructions, when executed by at least one processor of the fluid injector system, further cause the at least one processor to: open the second valve isolating the second drive component from the first fluid reservoir and the fluid conduit during a transition from the first phase of the injection protocol to the second phase of the injection protocol.

Clause 37: The computer program product of any of clauses 32 to 36, wherein the one or more instructions, when executed by at least one processor of the fluid injector system, further cause the at least one processor to: during the first phase of the injection protocol prior to transitioning to the second phase of the injection protocol, actuate the second drive component to pressurize the second fluid relative to a pressure of the first fluid in the fluid conduit.

Clause 38: The computer program product of clause 37, wherein the fluid injector system further comprises at least a first valve controlling fluid communication between the first reservoir and the fluid conduit and a second valve controlling fluid communication between the second reservoir and the fluid conduit, and wherein the one or more instructions, when executed by at least one processor of the fluid injector system, further cause the at least one processor to close the second valve prior to pressurizing the second fluid relative to the pressure of the first fluid in the fluid conduit.

Clause 39: The computer program product of any of clauses 32 to 38, wherein the one or more instructions, when executed by at least one processor of the fluid injector system, further cause the at least one processor to, during the first phase of the injection protocol prior to transitioning to the second phase of the injection protocol, adjust at least one property of the injection protocol to prevent backflow of the first fluid into the second fluid reservoir.

Clause 40: The computer program product of any of clauses 32 to 39, wherein adjusting at least one property of the injection protocol comprises at least one of: advancing the second drive component at a constant speed, linearly increasing a speed of the second drive component, and exponentially increasing the speed of the second drive component.

Clause 41: A method of performing an injection protocol comprising at least a first phase and a second phase using a fluid injector system, the second phase subsequent to the first phase, the method comprising: providing a control device operatively associated with a first drive component and a second drive component, the first drive component configured to pressurize and inject a first fluid from a first fluid reservoir through a fluid conduit, the second drive component configured to pressurize and inject a second fluid from a second fluid reservoir through the fluid conduit, actuating at least the first drive component to inject the first phase through the fluid conduit during the first phase of the injection protocol; actuating the second drive component to pressurize the second fluid relative to a pressure of the first fluid in the fluid conduit during the first phase of the injection protocol prior to transitioning to the second phase of the injection protocol; and actuating the second drive component to inject at least the second fluid through the fluid conduit so that a desired steady-state ratio of the first fluid and the second fluid in the second phase is reached during the second phase of the injection protocol.

Clause 42: The method of clause 41, wherein the first fluid comprises a contrast medium and the second fluid comprises a diluent.

Clause 43: The method of clause 41 or 42, wherein the desired steady-state ratio of the first fluid and the second fluid in the second phase is reached at a quicker rate than if the second drive component is not actuated prior to transitioning to the second phase of the injection protocol.

Clause 44: The method of any of clauses 41 to 43, further comprising ceasing actuation or reducing a speed of the first drive component during the first phase of the injection protocol prior to transitioning to the second phase of the injection protocol.

Clause 45: The method of any of clauses 41 to 44, further comprising adjusting a speed of the first drive component to inject the first fluid at a flow rate to reach the desired steady-state ratio of the first fluid and the second fluid through the fluid conduit during the second phase of the injection protocol.

Clause 46: The method of any of clauses 41 to 45, wherein the fluid injector system comprises at least a first valve controlling fluid communication between the first reservoir and the fluid conduit and a second valve controlling fluid communication between the second reservoir and the fluid conduit, and wherein the method further comprises closing the second valve prior to pressurizing the second fluid relative to the pressure of the first fluid in the fluid conduit.

Clause 47: The method of clause 46, further comprising opening the second valve isolating the second fluid reservoir from the first fluid reservoir and the fluid conduit during a transition from the first phase of the injection protocol to the second phase of the injection protocol.

Clause 48: The method of any of clauses 41 to 47, wherein pressurizing the second fluid relative to the pressure of the first fluid comprises selecting a pressure ratio of the pressure of the first fluid and a pressure of the second fluid to reach the desired steady-state flow ratio of the first fluid and the second fluid for the second phase.

Clause 49: The method of any of clauses 41 to 48, wherein pressurizing the second fluid relative to the pressure of the first fluid comprises gradually increasing a pressure of the second fluid such that, at a transition from the first phase of the injection protocol to the second phase of the injection protocol, the pressure of the second fluid is substantially equal to the pressure of the first fluid. The method of any of clauses 41 to 48, wherein pressurizing the second fluid relative to the pressure of the first fluid comprises gradually increasing a pressure of the second fluid such that at a transition from the first phase of the injection protocol to the second phase of the injection protocol, the pressure of the second fluid is 20% to 150% of the pressure of the first fluid.

Clause 50: The method of any of clauses 41 to 49, further comprising adjusting at least one property of the injection protocol to prevent backflow of the first fluid into the second fluid reservoir during the first phase of the injection protocol prior to transitioning to the second phase of the injection protocol.

Clause 51: The method of clause 50, wherein adjusting at least one property of the injection protocol comprises at least one of: advancing the second drive component at a constant speed, linearly increasing a speed of the second drive component, and exponentially increasing the speed of the second drive component.

Clause 52: A method of performing an injection protocol comprising at least a first phase and a second phase using a fluid injector system, the second phase subsequent to the first phase, the method comprising: providing a control device operatively associated with a first drive component and a second drive component, the first drive component configured to pressurize and inject a first fluid from a first fluid reservoir through a fluid conduit, the second drive component configured to pressurize and inject a second fluid from a second fluid reservoir through the fluid conduit, actuating at least one of the first drive component and the second drive component to inject at least one of the first fluid and the second fluid through the fluid conduit at a first desired steady-state ratio during the first phase of the injection protocol; actuating the first drive component and the second drive component to inject the first fluid and the second fluid through the fluid conduit such that a volumetric ratio of the second fluid displaced from the second fluid reservoir relative to the first fluid displaced from the first fluid reservoir exceeds a second desired steady-state ratio during an initial portion of the second phase of the injection protocol; and actuating at least one of the first drive component and the second drive component to reduce the volumetric ratio until the volumetric ratio reaches the second desired steady-state ratio of the first fluid and the second fluid in the second phase subsequent to the initial portion of the second phase.

Clause 53: The method of clause 52, wherein the first fluid comprises a contrast medium and the second fluid comprises a diluent.

Clause 54: The method of clause 52 or 53, wherein the second desired steady-state ratio of the first fluid and the second fluid in the second phase is reached at a quicker rate than if the actuation of the first drive component and the second drive component to inject the first fluid and the second fluid through the fluid conduit such that a volumetric ratio of the second fluid displaced from the second fluid reservoir relative to the first fluid displaced from the first fluid reservoir does not exceed a second desired steady-state ratio.

Clause 55: The method of any of clauses 52 to 54, further comprising ceasing actuation or reduce a speed of the first drive component during the first phase of the injection protocol prior to transitioning to the second phase of the injection protocol.

Clause 56: The method of any of clauses 52 to 55, wherein the fluid injector system further comprises at least a first valve controlling fluid communication between the first reservoir and the fluid conduit and a second valve controlling fluid communication between the second reservoir and the fluid conduit, and wherein the method further comprises opening the second valve isolating the second drive component from the first fluid reservoir and the fluid conduit during a transition from the first phase of the injection protocol to the second phase of the injection protocol.

Clause 57: The method of any of clauses 52 to 56, further comprising actuating the second drive component to pressurize the second fluid relative to a pressure of the first fluid in the fluid conduit during the first phase of the injection protocol prior to transitioning to the second phase of the injection protocol.

Clause 58: The method of clause 57, wherein the fluid injector system further comprises at least a first valve controlling fluid communication between the first reservoir and the fluid conduit and a second valve controlling fluid communication between the second reservoir and the fluid conduit, and wherein the method further comprises closing the second valve prior to pressurizing the second fluid relative to the pressure of the first fluid in the fluid conduit.

Clause 59: The method of any of clauses 52 to 58, further comprising adjusting at least one property of the injection protocol to prevent backflow of the first fluid into the second fluid reservoir during the first phase of the injection protocol prior to transitioning to the second phase of the injection protocol.

Clause 60: The method of clause 59, wherein adjusting at least one property of the injection protocol comprises at least one of: advancing the second drive component at a constant speed, linearly increasing a speed of the second drive component, and exponentially increasing the speed of the second drive component.

Further details and advantages of the various examples described in detail herein will become clear upon reviewing the following detailed description of the various examples in conjunction with the accompanying drawing figures.

DETAILED DESCRIPTION OF THE DISCLOSURE

Figure 1:
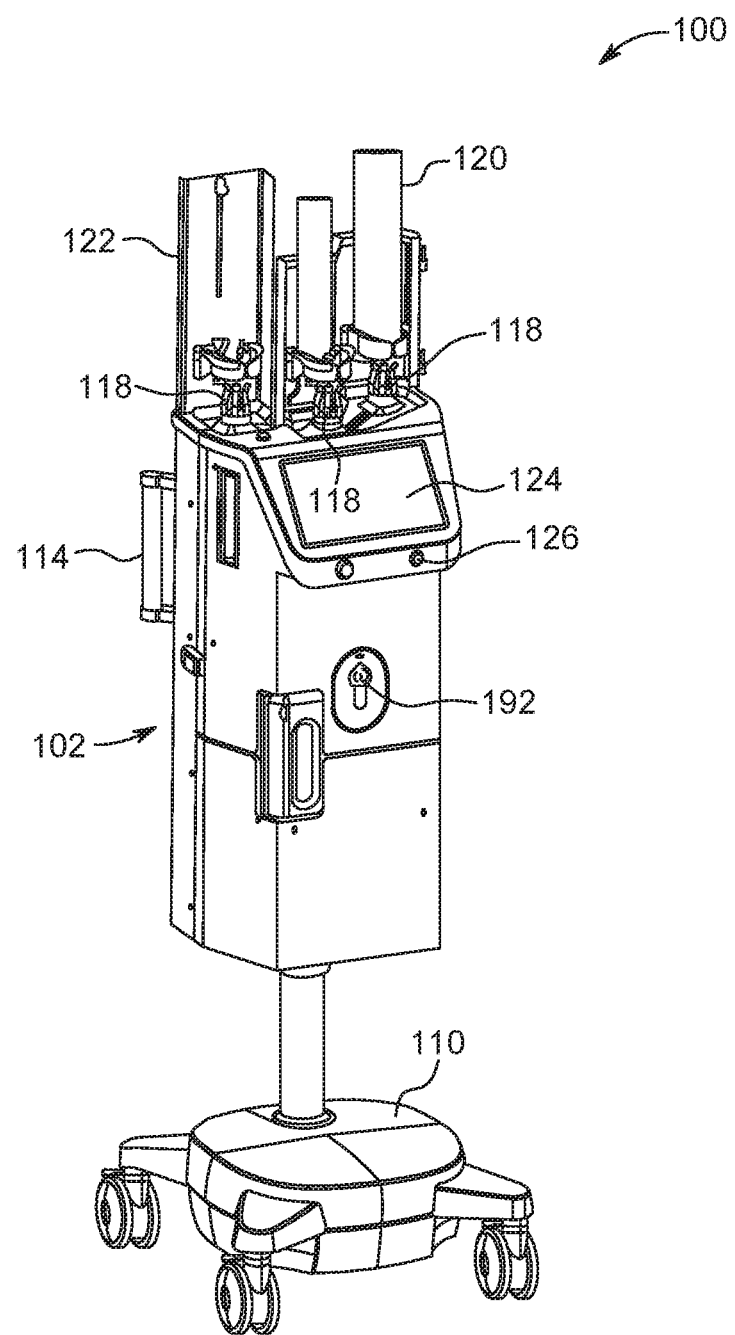
FIG. 1 is a perspective view of a fluid injector system according to one example of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to a syringe of a multi-patient disposable set, the term "proximal" refers to a portion of a syringe nearest a piston for delivering fluid from a syringe.

Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". The terms "approximately", "about", and "substantially" mean a range of plus or minus ten percent of the stated value.

As used herein, the term "at least one of" is synonymous with "one or more of". For example, the phrase "at least one of A, B, and C" means any one of A, B, and C, or any combination of any two or more of A, B, and C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C. Similarly, as used herein, the term "at least two of" is synonymous with "two or more of". For example, the phrase "at least two of D, E, and F" means any combination of any two or more of D, E, and F. For example, "at least two of D, E, and F" includes one or more of D and one or more of E; or one or more of D and one or more of F; or one or more of E and one or more of F; or one or more of all of D, E, and F.

It is also to be understood that the specific devices and processes illustrated in the attached drawings, and described in the following specification, are simply exemplary examples of the disclosure. Hence, specific dimensions and other physical characteristics related to the examples disclosed herein are not to be considered as limiting.

When used in relation to a fluid reservoir, such as a syringe, a rolling diaphragm, or multiple syringe disposable set, the term "distal" refers to a portion of the fluid reservoir nearest to a patient. When used in relation to a fluid reservoir, such as a syringe, a rolling diaphragm, or multiple syringe disposable set, the term "proximal" refers to a portion of the fluid reservoir nearest to the injector system.

The term "open", when used to refer to a fluid delivery component, means that the fluid reservoir is in fluid connection with an outlet to atmospheric pressure or connected to a patient's vascular system, for example through a nozzle or the open end of a tubing component or catheter. In an open system, fluid flow may be constrained or restricted, for example by forcing a fluid through a small diameter fluid path where flow may be determined by physical parameters of the system and the fluid, such as tubing diameter, fluid path constrictions, applied pressure, viscosity, etc. The term "closed" or "closeable", when used to refer to a fluid delivery component, means that the fluid reservoir has at least one state in which the component is not in fluid connection with an outlet under atmospheric pressure or connected to a patient's vascular system or the fluid in the fluid reservoir is fluidly isolated, for example where fluid flow is stopped by a valve, such as a stopcock, high crack pressure valve, pinch valve, and the like, that closes a fluid pathway.

As used herein, the terms "capacitance" and "impedance" are used interchangeably to refer to a volumetric expansion of fluid reservoirs, syringes, fluid lines, and/or other components of a fluid delivery system as a result of pressurized fluids with such components. Capacitance and impedance may be due to high injection pressures, which may be on the order of 1,200 psi in some angiographic procedures, and may result in a volume of fluid in excess of the desired quantity selected for the injection procedure.

Referring to the drawings in which like reference characters refer to like parts throughout the several views thereof, one aspect or example of the present disclosure is generally directed to a multi-fluid medical injector/injector system 100 (hereinafter "fluid injector system 100") which in certain embodiments may include a multi-use disposable set (MUDS) 130 configured for delivering fluid to a patient using a single-use disposable set (SUDS) 190 connector and in other embodiments may include two or more disposable fluid reservoirs or syringes, which may be disposed after one injection procedure or a specific number of injection procedures. The fluid injector system 100 may include multiple components as individually described herein. Generally, the fluid injector system 100 depicted in FIGS. 1-2 has a powered injector or other administration device and a fluid delivery set intended to be associated with the injector to deliver one or more fluids from one or more multi-dose containers under pressure into a patient, as described herein. The various devices, components, and features of the fluid injector system 100 and the fluid delivery set associated therewith are likewise described in detail herein. While the various examples of the methods and processes are shown with reference to an injector system having a multi-use disposable set ("MUDS") and a single-use disposable set ("SUDS") configuration in FIGS. 1-2, the disclosure is not limited to such an injector system and may be utilized in other syringe based injector systems, such as but not limited to those described in U.S. Pat. Nos. 7,553,294, 7,563,249, 8,945,051, 9,173,995, 10,124,110; and U.S. application Ser. Nos. 15/305,285, 15/541,573, 15/568,505; the disclosures of each of which are incorporated herein in their entirety by this reference.

With reference to FIG. 1, a fluid injector system 100 according to one example includes an injector housing 102 that encloses the various mechanical drive components, electrical and power components necessary to drive the mechanical drive components, and control components, such as electronic memory and electronic control devices, used to control operation of reciprocally movable pistons 103 (not shown) associated with the fluid injector system 100 described herein. Such pistons 103 may be reciprocally operable via electro-mechanical drive components such as a ball screw shaft driven by a motor, a voice coil actuator, a rack-and-pinion gear drive, a linear motor, and the like.

The fluid injector system 100 may include at least one bulk fluid connector 118 for connection with at least one bulk fluid source 120. In some examples, a plurality of bulk fluid connectors 118 may be provided. For example, as shown in the fluid injector embodiment illustrated in FIG. 1, three bulk fluid connectors 118 may be provided in a side-by-side or other arrangement. In some examples, the at least one bulk fluid connector 118 may include a spike configured for removably connecting to the at least one bulk fluid source 120, such as a vial, a bottle, or a bag. The at least one bulk fluid connector 118 may be formed on the multi-use disposable set ("MUDS"), as described herein. The at least one bulk fluid source 120 may be configured for receiving a medical fluid, such as saline, Ringer's lactate, an imaging contrast medium solution, or other medical fluid, for delivery to the patient by the fluid injector system 100.

Figure 2:
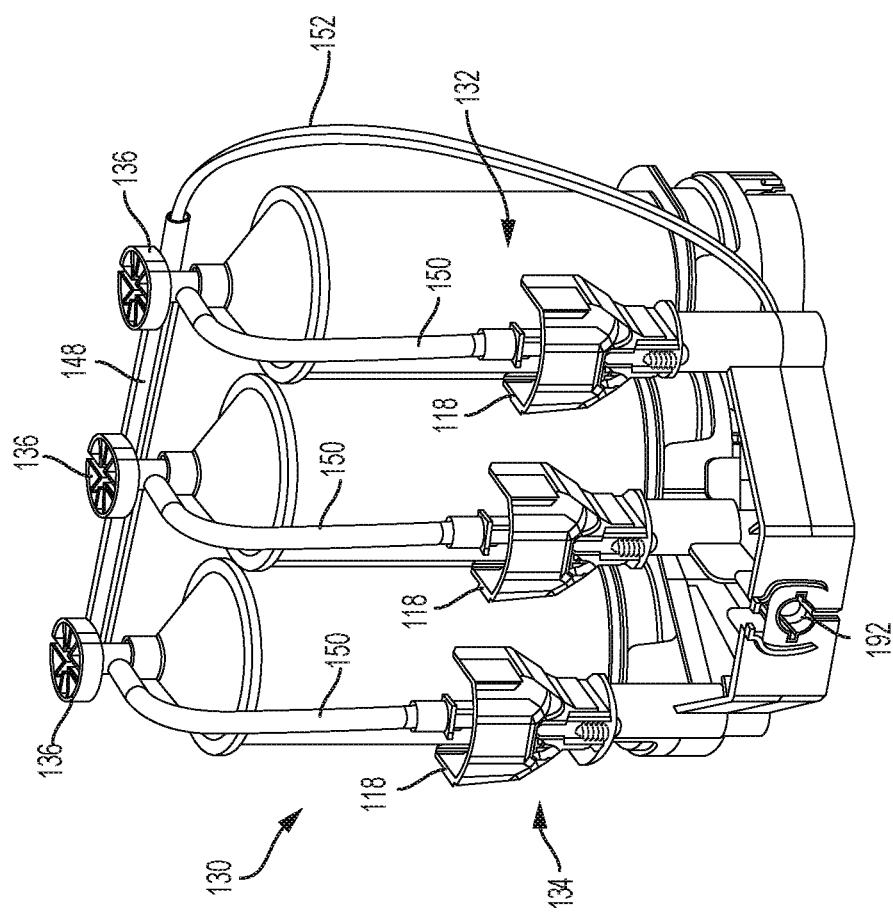
FIG. 2 is a perspective view of a multi-use disposable set for use with a fluid injector system of FIG. 1.

With reference to FIG. 2, a MUDS 130 is configured for being removably connected to the fluid injector system 100 for delivering one or more fluids from the one or more bulk fluid sources 120 to the patient. Examples and features of embodiments of the MUDS are further described in PCT International Publication No. WO 2016/112163, filed on Jan. 7, 2016, the disclosure of which is incorporated herein by reference in its entirety. The MUDS 130 may include one or more fluid reservoirs, such as one or more syringes 132. As used herein, the term "fluid reservoir" means any container capable of taking in and delivering a fluid, for example during a fluid injection procedure including, for example a syringe, a rolling diaphragm, a pump, a compressible bag, and the like. Fluid reservoirs may include the interior volume of at least a portion of a fluid pathway, such as one or more tubing lengths, that are in fluid communication with the interior of the fluid reservoir, including fluid pathway portions that remain in fluid communication with the fluid reservoir after the system is closed or fluidly isolated from the remainder of the fluid pathway. In some examples, the number of fluid reservoirs may correspond to the number of bulk fluid sources 120 (shown in FIG. 1). For example, with reference to FIG. 2, the MUDS 130 has three syringes 132 in a side-by-side arrangement such that each syringe 132 is fluidly connectable to one or more of the corresponding three bulk fluid sources 120. In some examples, one or more bulk fluid sources 120 may be connected to one or more syringes 132 of the MUDS 130. Each syringe 132 may be fluidly connectable to one of the bulk fluid sources 120 by a corresponding bulk fluid connector 118 and an associated MUDS fluid path 134. The MUDS fluid path 134 may have a spike element that connects to the bulk fluid connector 118 and the fluid line 150. In some examples, the bulk fluid connector 118 may be provided directly on the MUDS 130.

With continued reference to FIGS. 1 and 2, the MUDS 130 may include one or more valves 136, such as stopcock valves, for controlling which medical fluid or combinations of medical fluids are withdrawn from the multi-dose bulk fluid source 120 (see FIG. 1) into the fluid reservoirs 132 and/or are delivered to a patient from each fluid reservoir 132. In some examples, the one or more valves 136 may be provided on a distal end of the plurality of syringes 132 or on a manifold 148. The manifold 148 may be in selectable fluid communication via valves 136 with the interior volume of the syringes 132. The interior volume of the syringes 132 may be in selectable fluid communication via valves 136 with a first end of the MUDS fluid path 134 that connects each syringe 132 to the corresponding bulk fluid source 120. The opposing second end of the MUDS fluid path 134 may be connected to the respective bulk fluid connector 118 that is configured for fluidly connecting with the bulk fluid source 120. Depending on the position of the one or more valves 136, fluid may be drawn into the interior volume of the one or more syringes 132 or it may be delivered from the interior volume of the one or more syringes 132. In a first position, such as during the filling of the syringes 132, the one or more valves 136 are oriented such that fluid flows from the bulk fluid source 120 into the desired syringe 132 through a fluid inlet line 150, such as a MUDS fluid path. During the filling procedure, the one or more valves 136 are positioned such that fluid flow through one or more fluid outlet lines 152 or manifold 148 is blocked or closed. In a second position, such as during a fluid delivery procedure, fluid from one or more syringes 132 is delivered to the manifold 148 through the one or more fluid outlet lines 152 or syringe valve outlet ports. During the delivery procedure, the one or more valves 136 are positioned such that fluid flow through one or more fluid inlet lines 150 is blocked or closed. In a third position, the one or more valves 136 are oriented such that fluid flow through the one or more fluid inlet lines 150 and the one or more fluid outlet lines 152 or manifold 148 is blocked or closed. Thus, in the third position, each of the one or more valves 136 isolates the corresponding syringe 132 and prevents fluid flow into and out of the interior volume of the corresponding syringe 132. As such, each of the one or more syringes 132 and the corresponding valve 136 defines a closed system.

The one or more valves 136, fluid inlet lines 150, and/or fluid outlet lines 152 may be integrated into or in fluid communication via the manifold 148. The one or more valves 136 may be selectively positioned to the first or second position by manual or automatic handling. For example, the operator may position the one or more valves 136 into the desired position for filling, fluid delivery, or the closed position. In other examples, at least a portion of the fluid injector system 100 is operable for automatically positioning the one or more valves 136 into a desired position for filling, fluid delivery, or the closed position based on input by the operator or by a protocol executed by the electronic control unit.

With continued reference to FIGS. 1 and 2, according to the described embodiment the fluid injector system 100 may have a connection port 192 that is configured to form a releasable fluid connection with at least a portion of the SUDS 190. In some examples, the connection port 192 may be formed on the MUDS 130. As described herein, the SUDS 190 may be connected to the connection port 192, formed on at least a portion of the MUDS 130 and/or the housing 102. Desirably, the connection between the SUDS 190 and the connection port 192 is a releasable connection to allow the SUDS 190 to be selectively connected to and disconnected from the connection port 192. In some examples, the SUDS 190 may be disconnected from the connection port 192 and disposed after each fluid delivery procedure, and a new SUDS 190 may be connected to the connection port 192 for a subsequent fluid delivery procedure. The SUDS 190 may be used to deliver one or more medical fluids to a patient by SUDS fluid line 208 having a distal end that may be selectively disconnected from the body of the SUDS 190 and connected to a patient catheter. Other examples and features of the SUDS 190 are described in U.S. Patent Publication No. 2016/0331951, filed Jul. 7, 2016, the disclosure of which is incorporated herein by reference.

Referring again to FIG. 1, the fluid injector system 100 may include one or more user interfaces 124, such as a graphical user interface (GUI) display window. The user interface 124 may display information pertinent to a fluid injection procedure involving fluid injector system 100, such as injection status or progress, current flow rate, fluid pressure, and volume remaining in the at least one bulk fluid source 120 connected to the fluid injector system 100 and may be a touch screen GUI that allows an operator to input commands and/or data for operation of fluid injector system 100. Additionally, the fluid injector system 100 and/or user interface 124 may include at least one control button 126 for tactile operation by an attendant operator of the fluid injector system 100. The at least one control button 126 may be a graphical part of the user interface 124, such as a touch screen.

Figure 3:
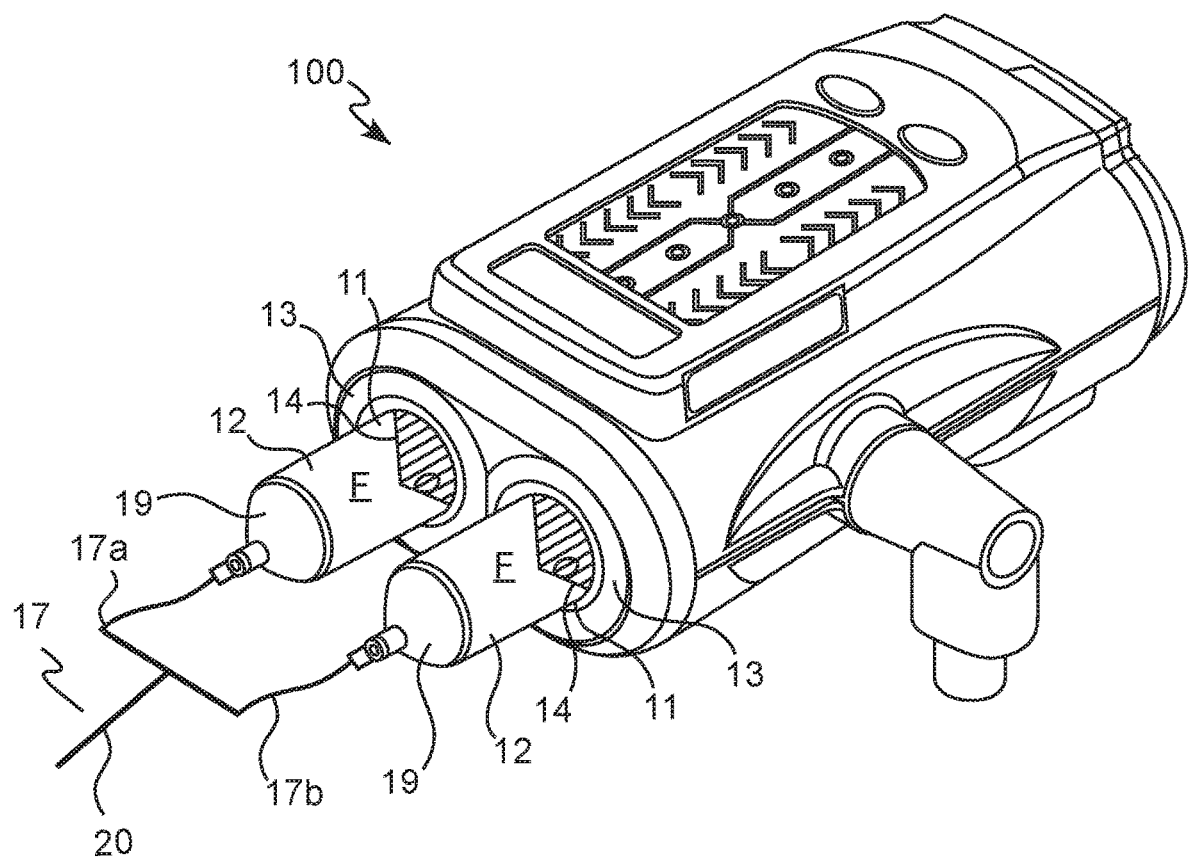
FIG. 3 is a perspective view of a fluid injector system according to another example of the present disclosure.

While FIGS. 1-2 illustrate one example of a fluid injector system 100 and associated components and structure, it is to be understood that the present disclosure is not limited to any particular type or variety of the fluid injector system 100. Referring now to FIG. 3, another non-limiting example of a fluid injector system 100 in accordance with the present disclosure includes at least one fluid reservoir, such as syringe 12, at least one piston 103 (see FIG. 4) connectable to at least one plunger 14, and a fluid control module (not pictured). The at least one syringe 12 is generally adapted to interface with at least one component of the system, such as a syringe port 13. The fluid injector system 100 is generally configured to deliver at least one fluid F to a patient during an injection procedure. The fluid injector system 100 is configured to releasably receive the at least one syringe 12, which is to be filled with at least one fluid F, such as a contrast media, saline solution, Ringer's lactate, or any desired medical fluid. The system may be a multi-syringe injector, wherein several syringes may be oriented side-by-side or in another spatial relationship and are separately actuated by respective pistons associated with the injector. The at least one syringe 12 may be oriented in any manner such as upright, downright, or positioned at any degree angle. In another embodiment, a fluid injector 100 may interface with one or more rolling diaphragm syringes (not shown). Non-limiting examples of rolling diaphragm syringe based injectors are described in U.S. application Ser. Nos. 15/305,285, and 15/568,505 and PCT International Application No. PCT/US2017/056747, the disclosures of which are incorporated herein.

Figure 4:
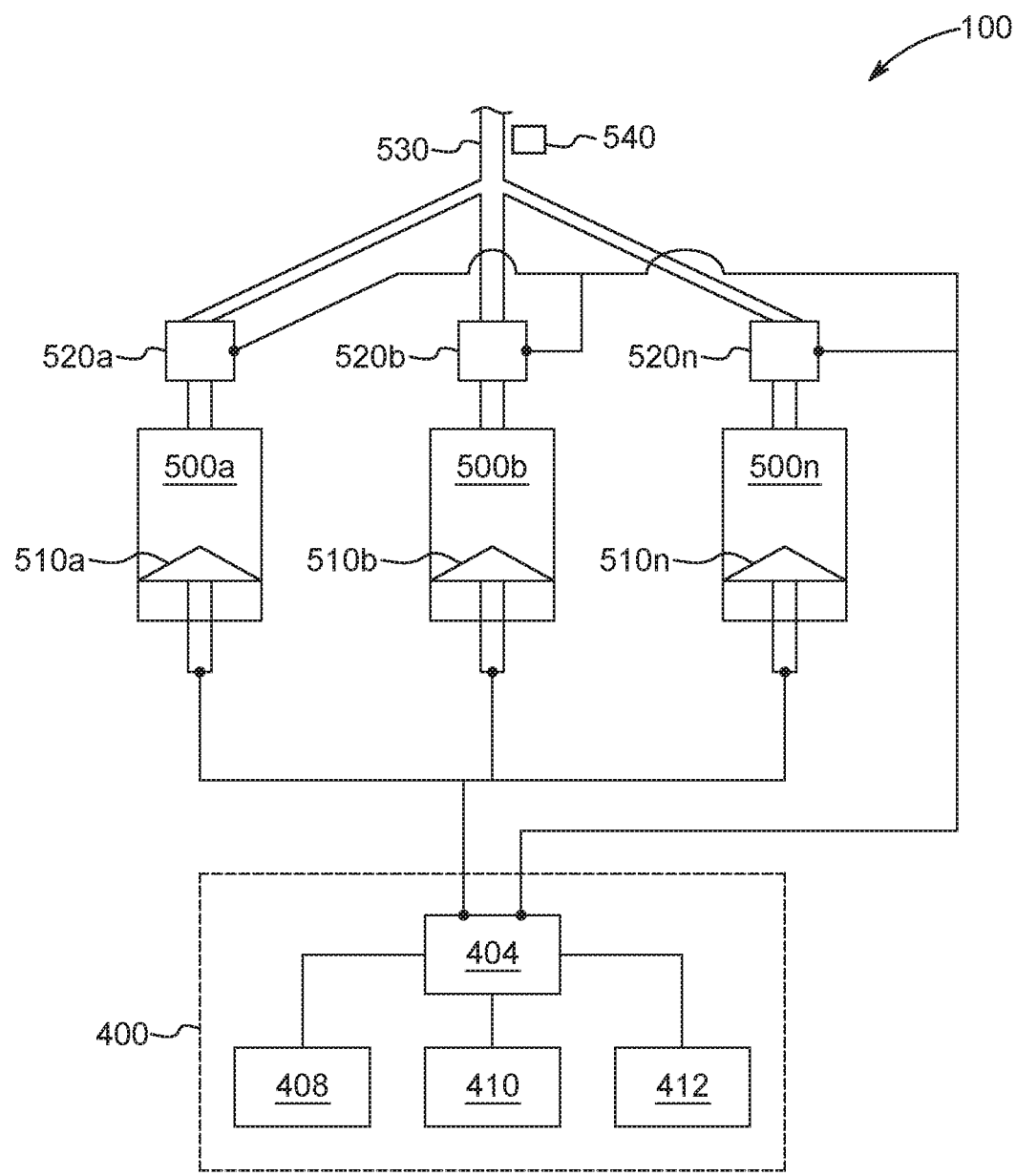
FIG. 4 is a schematic view of an electronic control system of a fluid injector system in accordance with examples of the present disclosure.

With continued reference to FIG. 3, the injector system 100 may be used during a medical procedure to inject the at least one medical fluid F into the vasculature system of a patient by driving a plunger 14 of at least one syringe 12 with a drive member, such as the at least one piston 103 (see FIG. 4). The at least one piston may be reciprocally operable upon at least a portion of the at least one syringe, such as the plunger 14. Upon engagement, the at least one piston may move the plunger 14 toward the distal end 19 of the at least one syringe, as well as retracting the plunger 14 toward the proximal end 11 of the at least one syringe 12.

A tubing set 17 (e.g., first and second fluid conduits 17a and 17b, and common fluid conduit 20) may be in fluid communication with an outlet port of each syringe 12 to place each syringe in fluid communication with a catheter for delivering the fluid F from each syringes 12 to the catheter (not shown) inserted into a patient at a vascular access site. The first and second fluid conduits 17a and 17b may be connected to the common fluid conduit 20 by any suitable mechanism known in the art (e.g., a Y-connector or a T-connector). The fluid injector system 100 shown in FIG. 3 is an open system do to the lack of valves capable of isolating the syringes 12 from one another and from at least a portion of the tubing set 17. However, it is to be understood that valves, similar or identical to the valves 136 described with reference to the fluid injector system 100 of FIGS. 1 and 2, may be added distally of the syringes 12 to convert fluid injector system 100 of FIG. 3 to a closed system.

Referring now to FIG. 4, fluid injector systems 100 in accordance with the present disclosure may be associated with and controlled by an electronic control device 400 configured to execute one or more injector protocols including, for example, the filling, priming, and delivery operations. In some examples, the electronic control device 400 may control the operation of various valves, stopcocks, piston members, and other elements to affect a desired gas/air removal, filling, and/or delivery procedure. The electronic control device 400 may include at least one processor 404, memory 408, an input component 410, and an output component 412. The electronic control device further may include a bus that permits communication among the components of electronic control device 400. The at least one processor 404 may be implemented in hardware, firmware, or a combination of hardware and software. For example, processor 904 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 408 may include a hard disk (e.g., a magnetic disk, an optical disk, a magneto-optic disk, a solid state disk, etc.) and/or another type of computer-readable medium. The input component 410 may include a component that permits the electronic control device 400 to receive information, such as via user input (e.g., the user interface 124). The output component 412 may include a component that provides output information from the electronic control device 400 (e.g., the user interface 124).

The electronic control device 400 may be programmed or configured to perform one or more processes and/or methods based on the at least one processor 404 executing software instructions stored by a computer-readable medium, such as memory 408. When executed, software instructions stored in memory 408 may cause the at least one processor 404 to perform one or more processes and/or methods described herein.

With continued reference to FIG. 4, the electronic control device 400, more particularly the at least one processor 404, may be in operative communication with one or more components of the fluid injector system 100 to control an operation of the fluid injector system 100. The electronic control device 400 may be in operative communication with one or more drive components 510a, 510b, 510n respectively associated with one or more fluid reservoirs 500a, 500b, 500n of the fluid injector system 100 to control filling of fluid and delivery of fluid from the fluid reservoirs 500a, 500b, 500n. More particularly, each of the one or more drive components 510a, 510b, 510n may be associated with one of the fluid reservoirs 500a, 500b, 500n such that fluid contained in each of the fluid reservoirs 500a, 500b, 500n may be selectively delivered via actuation of the associated drive component 510a, 510b, 510n. The fluid reservoirs 500a, 500b, 500n may be, or may correspond to, the syringes 132 of the fluid injector system 100 of FIGS. 1-2 and/or the syringes 12 of the fluid injector system 100 of FIG. 3 or other syringe-type structures, such as rolling diaphragm syringes, as described herein. The one or more drive components 510a, 510b, 510n may be, or may correspond to, the pistons 103 of the fluid injector systems 100 of FIGS. 1-3. The one or more fluid reservoirs 500a, 500b, 500n may be in fluid communication with a fluid conduit 530 for delivering fluid to a catheter or other component connected to a patient. The fluid conduit 530 may be, or may correspond to, the SUDS 190 of the fluid injector system 100 of FIGS. 1-2 and/or the tubing set 17 of the fluid injector system 100 of FIG. 3

In aspects and examples of a closed fluid injector system 100 (e.g., the fluid injector system 100 of FIGS. 1 and 2), the electronic control device 400 further may be in operative communication with one or more valves 520a, 520b, 520n in order to rotate or otherwise actuate the valves 520a, 520b, 520n to direct flow into or out of and/or isolate flow from one or more of the fluid reservoirs 500a, 500b, 500n to the fluid conduit 530. The valves 520a, 520b, 520n may be, or may correspond to, the valves 136 described herein in connection with FIG. 2.

In some aspects and examples, the at least one processor 404 may be programmed or configured to execute an injection protocol including a first phase and at least a second phase. Each of the first phase and the second phase of the injection protocol include or define a desired steady-state ratio of a first fluid relative to a second fluid. According to various embodiments, the steady-state ratio for each phase may range from 100:0 of the first fluid to the second fluid to 0:100 of the first fluid to the second fluid, inclusive of any intermediate ratios. As described herein, the desired steady-state ratio is based on volume component of the first fluid relative to the volume component of the second fluid, although mass, density, viscosity, flow rate, or another characteristic of the fluids may also be the basis of the desired steady-state ratio. In various embodiments, the first fluid may be an imaging contrast solution and the second fluid may be a flushing fluid, such as saline or Ringer's Lactate.

In some aspects or examples, the first fluid may be contained in a first fluid reservoir 500a and the second fluid may be contained in a second fluid reservoir 500b. It should be understood that the order of the various fluid reservoirs may be changed, for example, in certain embodiments the first fluid reservoir may be reservoir 500b and the second fluid reservoir may be 500a without deviating from the scope of the present disclosure. In certain embodiments, the third fluid reservoir 500n may contain a third fluid or an additional volume of the first or second fluids, or a different concentration of the first or second fluid. The desired steady-state ratios for the first and second phases of the injection protocol may be reached by selectively and independently actuating the first and second drive components 510a, 510b associated with the first and second fluid reservoir 500a, 500b and optionally actuating a third drive component 510n associated with a third fluid reservoir 500n. For example, if the desired steady-state ratio is 50% of the first fluid to 50% of the second fluid, the first and second drive components 510a, 510b associated with the first and second fluid reservoir 500a, 500b may be actuated, by the at least one processor 404, at the same speed to facilitate equal delivery of the first and second fluids. Similarly, if the desired steady-state ratio is 75% of the first fluid to 25% of the second fluid, the first drive component 510a associated with the first fluid reservoir 500a may be actuated at three times the speed of the second drive component 510b associated with the second fluid reservoir 500b to facilitate delivery of a 3:1 ratio of the first fluid relative to the second fluid. If the desired steady-state ratio is 100% of the first fluid to 0% of the second fluid, the first drive component 510a associated with the first fluid reservoir 500a is actuated and the second drive component 510b associated with the second fluid reservoir 500b is not actuated. In aspects or examples of the present disclosure, the first fluid may be contrast or another diagnostic imaging fluid, and the second fluid may be a diluent such as saline, Ringer's lactate, a mixture of contrast diluted with saline, or the like. The terms "contrast" and "diluent" may be used herein to refer to the first fluid and second fluid, respectively, when describing specific aspects or examples of the present disclosure. However, it is to be understood that embodiments of the present disclosure are not limited to using contrast and diluent as the first and second fluids.

However, when the controller instructs the various drive components to drive as a specific rate to achieve a desired steady-state fluid ratio, the observed initial fluid ratio may differ from the desired steady-state ratio due to one or more fluid flow factors (e.g., fluid ratio of the previous phase, differences in the densities and/or viscosities of the first and at least the second fluids, impedance and/or capacitance of the one or more fluid reservoirs 500a, 500b, 500n and the fluid conduit 530, and/or fluid dynamics within the fluid reservoirs 500a, 500b, 500n and the fluid conduit 530), and the actual ratio of the first and second fluid delivered to the patient may not be reflective of the desired steady-state ratio. Aspects or examples of the present disclosure are directed to fluid injector systems, computer program products, and methods of compensating for these fluid flow factors so that the initially observed fluid ratio more quickly and closely matches the desired fluid ratio.

In some aspects of examples, the ratio of the first fluid relative to the second fluid may be measured by a ratio sensor 540 associated with the fluid conduit 530 downstream of the first and second fluid reservoirs 500a, 500b. The ratio sensor 540 may be operatively connected to the at least one processor 404. In this manner, the first and second drive components 510a, 510b associated with the first and second fluid reservoir 500a, 500b may be actuated, by the at least one processor 404, at a desired speed to achieve a desired ratio of the first and second fluids, as sensed by the ratio sensor 540. Based on a sensed density, the at least one processor 404 may increase or decrease the speed of the first and second drive components 510a, 510b such that the actual fluid ratio sensed by the ratio sensor 540 is substantially equal to a desired ratio. In some aspects of examples, the ratio sensor 540 may be a density sensor configured for sensing a density of the fluid(s) flowing through the fluid conduit 530. In other aspects of examples, the ratio sensor 540 may be a viscosity sensor configured for sensing a viscosity of the fluid(s) flowing through the fluid conduit 530. In some aspects of examples, the ratio sensor 540 may be a light refraction sensor configured for sensing a ratio of the fluid(s) flowing through the fluid conduit 530 based on light refraction properties of the fluid(s). In further aspects or examples, the ratio sensors 540 may be a plurality of ratio sensors 540, including any combination of one or more of density sensors, viscosity sensors, and light refraction sensors.

Figure 5:
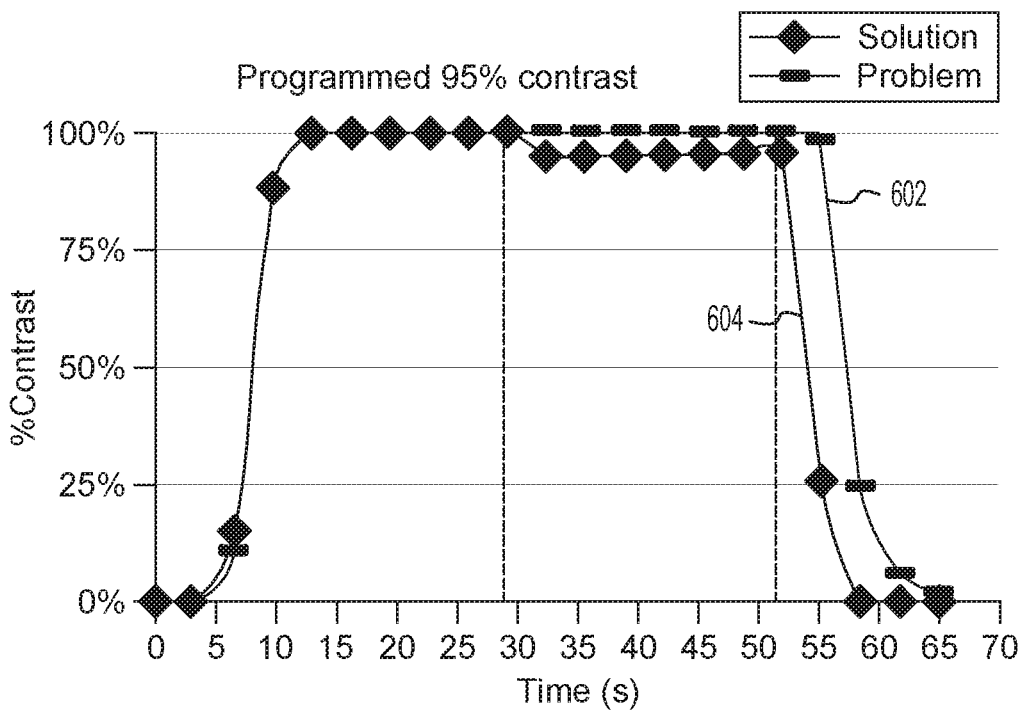
FIG. 5 is a graph comparing actual fluid delivery of prior art fluid injector systems to actual fluid delivery of a fluid injector system according to the present disclosure, for an injector protocol having a first phase of 100% contrast and a second phase of 95% contrast to 5% saline.

FIGS. 5-8 illustrate flow ratio curves according to aspects or examples of the present disclosure, which account for the above fluid flow factors, compared to flow ratio curves of prior art fluid injector systems. Referring now to FIG. 5, flow ratio curves are shown for an injection protocol including a first phase having a desired steady-state ratio of 100% of the first fluid, such as contrast to 0% of the second fluid, such as a saline diluent, and a second phase having a desired steady-state ratio of 95% of the first fluid to 5% of the second fluid. The first phase injection occurs from approximately 0 seconds to approximately 29 seconds, while the second phase occurs from approximately 29 seconds into the injection to approximately 52 seconds. Flow ratio curve 602 illustrates the actual observed ratio of first fluid to the second delivered to the patient during the operation of certain prior art fluid injector systems and protocols. Flow ratio curve 604 illustrates the actual ratio of contrast to diluent delivered to the patient during the operation of the fluid injector system 100 according to various protocols of the present disclosure. As can be appreciated from FIG. 5, the flow ratio curve 602 never reaches the desired steady-state ratio of 95% contrast to 5% diluent due to one or more of the fluid flow factors described herein. In contrast, the flow ratio curve 604 reaches the desired steady-state ratio of 95% contrast to 5% diluent at approximately 32 seconds by performing one or more of the processes and/or methods described herein (see FIGS. 12 and 13).

Figure 6:
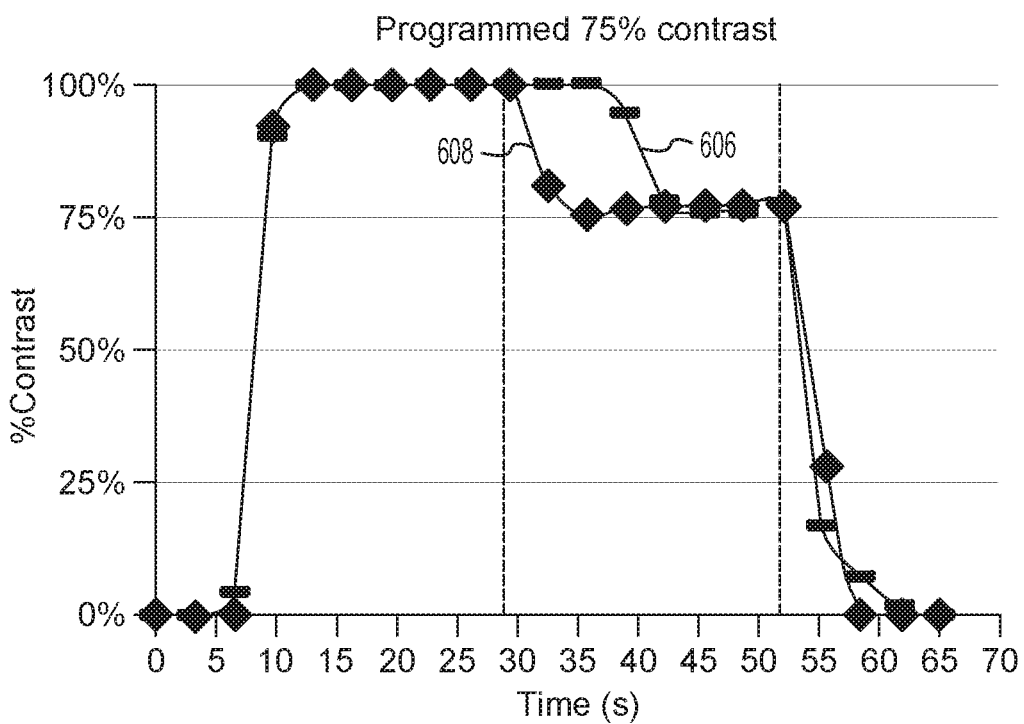
FIG. 6 is a graph comparing actual fluid delivery of prior art fluid injector systems to actual fluid delivery of a fluid injector system according to the present disclosure, for an injector protocol having a first phase of 100% contrast and a second phase of 75% contrast to 25% saline.
Figure 7:
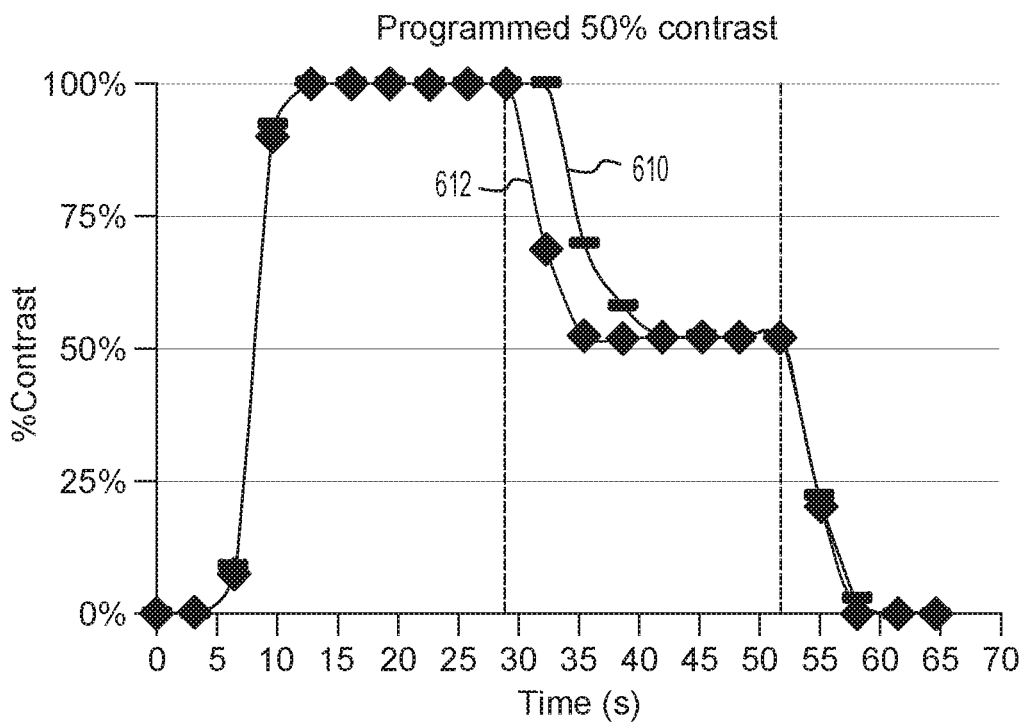
FIG. 7 is a graph comparing actual fluid delivery of prior art fluid injector systems to actual fluid delivery of a fluid injector system according to the present disclosure, for an injector protocol having a first phase of 100% contrast and a second phase of 50% contrast to 50% saline.
Figure 8:
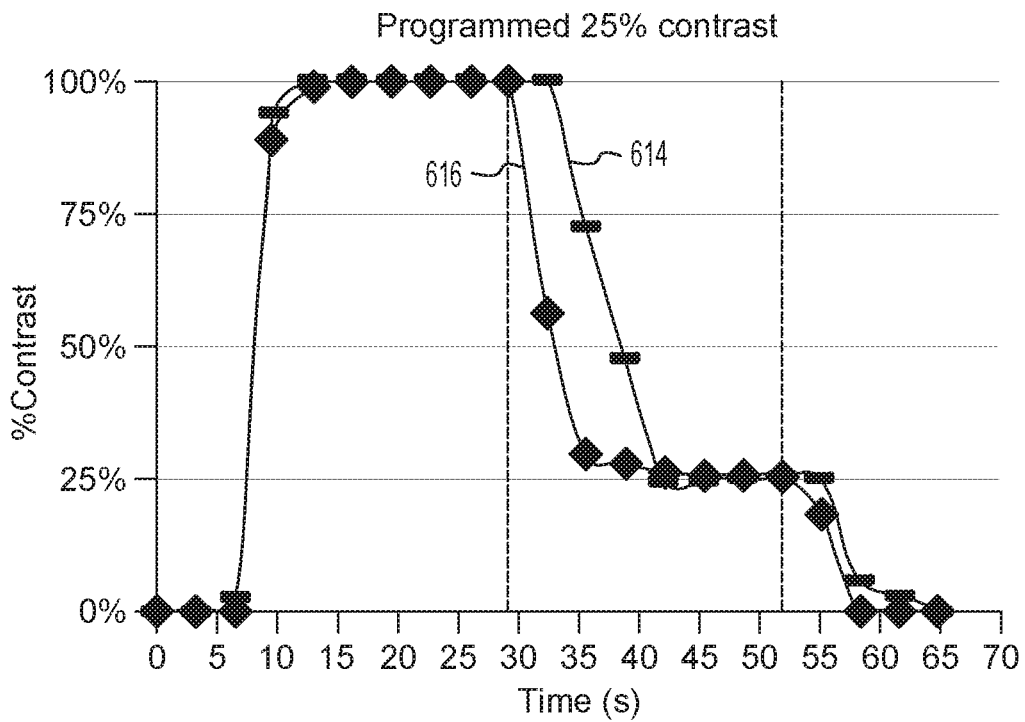
FIG. 8 is a graph comparing actual fluid delivery of prior art fluid injector systems to actual fluid delivery of a fluid injector system according to the present disclosure, for an injector protocol having a first phase of 100% contrast and a second phase of 25% contrast to 75% saline.

Similar to FIG. 5, FIGS. 6-8 illustrate flow ratio curves for various injection protocol having the first phase occurring from approximately 0 seconds to approximately 29 seconds, and the second phase occurring from approximately 29 seconds to approximately 52 seconds. In FIG. 6-8, flow ratio curves 606, 610, 614 illustrate the actual ratio of the first fluid (e.g., contrast) to the second fluid (e.g., diluent) that is delivered to the patient during the operation of certain prior art fluid injector systems and protocols, while flow ratio curves 608, 612, 616 illustrate the actual ratio of the first fluid (e.g., contrast) to the second fluid (e.g., diluent) delivered to the patient during the operation of the fluid injector system 100 according to the present disclosure. The first phase of the injection protocols of each of FIGS. 6-8 has a desired steady-state ratio of 100% contrast to 0% diluent. The second phase of the injection protocol of FIG. 6 has a desired steady-state ratio of 75% contrast to 25% diluent; the second phase of the injection protocol of FIG. 7 has a desired steady-state ratio of 50% contrast to 50% diluent; and the second phase of the injection protocol of FIG. 8 has a desired steady-state ratio of 25% contrast to 75% diluent. As may be appreciated from FIGS. 6-8, the flow ratio curves 606, 610, 614 corresponding to the prior art fluid injector systems take longer to reach the desired steady-state ratio of the second phase as compared to the flow ratio curves 608, 612, 616 corresponding to the fluid injector system 100 of the present disclosure. While the examples illustrated in FIGS. 5-8 illustrate injection protocols where the first phase is 100% contrast to 0% diluent, other ratios of the first fluid to the second fluid may be used in the first phase of the injection protocols and similar delays in the second phase reaching the desired steady-state flow ratios are also observed using conventional injection protocols, whereas using protocols that account for the one or more fluid flow factors as described herein reach the steady-state fluid flow ratio in significantly reduced times. Similar reductions in times to reach steady-state for a third fluid phase are also observed using the various protocols that account for the one or more fluid flow factors as described herein are also observed.

Figure 12:
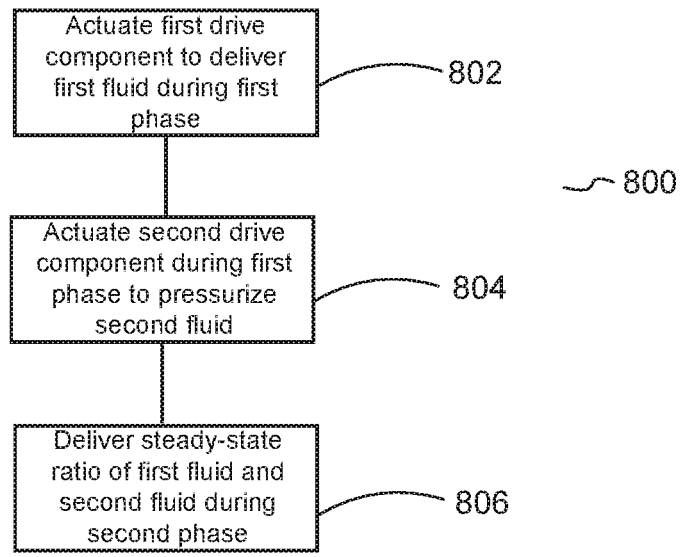
FIG. 12 is a step sequence diagram of a method of improving ratio performance of a first fluid and a second fluid during a multi-phase injection protocol using a fluid injector system according to one example of the present disclosure.
Figure 13:
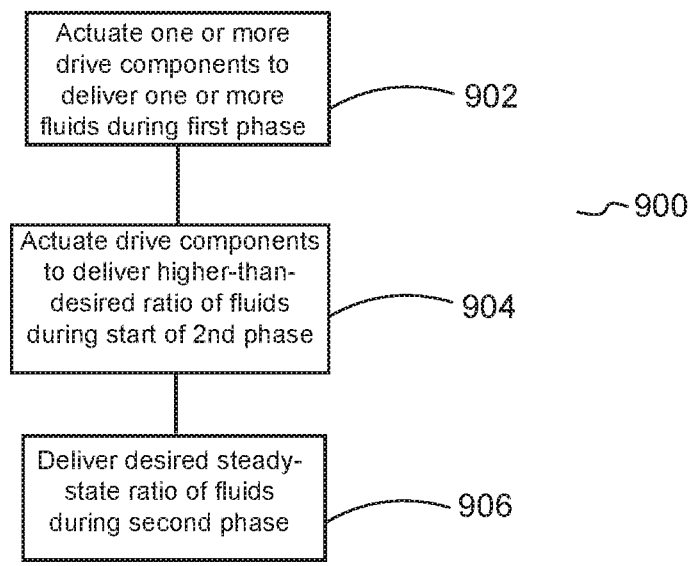
FIG. 13 is a step sequence diagram of a method of improving ratio performance of a first fluid and a second fluid during a multi-phase injection protocol using a fluid injector system according to another example of the present disclosure.

The reduction in time to reach the desired steady-state pressure ratio of the second phase of flow ratio curves 608, 612, 616 ensures that the volumetric ratio of the first fluid relative to the second fluid actually delivered to the patient is substantially consistent with the programmed injection protocol. Referring now to FIGS. 12 and 13, methods 800 and 900 for performing the injection protocol to decrease the time required to reach the desired steady-state ratio of the second phase will now be described. In some aspects or examples, each of the methods 800 and 900 may be performed by the at least one processor 404 of the fluid injector system 100 as described herein with reference to FIGS. 1-4. In some aspects or examples, each of the methods 800 and 900 may be stored as instructions in a non-transitory computer-readable media, such as memory 408 of FIG. 4, such that the instructions, when executed by the at least one processor 404, cause the at least one processor 404 to perform the method 800 and/or the method 900.

First referring to FIG. 12, at step 802 the method 800 may include, during the first phase of the injection protocol, actuating at least the first drive component 510a to inject the fluid prescribed in the first phase. To provide clarity of the present disclosure and for simplicity, the following methods describe an injection protocol where the first phase is 100% of the first fluid and 0% of the second fluid, Actuation of the first drive component 510a pressurizes the first fluid reservoir 500a and injects the first fluid into the fluid conduit 530 and ultimately to the patient. In some aspects or examples, the first phase of the injection protocol is a dual flow phase including both the first fluid and the second fluid and includes the second fluid in addition to the first fluid, in which case the second drive component 510b is actuated to pressurize and inject the second fluid from the second fluid reservoir 500b. Similarly, additional fluids prescribed in the first phase of the injection protocol may be pressurized and injected from the additional fluid reservoirs 500n by actuating the associated additional drive components 510n. Actuating any of the drive components 510a, 510b, 510n may include distally advancing the drive component 510a, 510b, 510n to reduce the internal volume of the associated fluid reservoir 500a, 500b, 500n. Drive components 510a, 510b, 510n may be advanced at a constant speed, at a linearly increasing or decreasing speed, at an exponentially increasing or decreasing speed, or any other speed profile. Actuation of the one or more drive components 510a, 510b, 510n may be controlled by the at least one processor 440.

In aspects or examples in which the fluid injector system 100 is a closed system, the method 800 further may include closing the second valve 520b prior to step 802 to prevent flow from the fluid conduit 530 into the second fluid reservoir 500b.

With continued reference to FIG. 12, the method 800 further may include, at step 804, during the first phase of the injection protocol prior to transitioning to the second phase of the injection protocol, actuating the second drive component 510b to pressurize the second fluid in the second fluid reservoir 500b relative to a pressure of the first fluid injected into in the fluid conduit 530 at step 802. In aspects or examples in which the fluid injector system 100 is a closed system, the method 800 further may include opening the second valve 520b prior to step 804 to allow fluid communication between the second fluid reservoir 500b and the fluid conduit 530.

In aspects or examples in which the first phase includes the injection of multiple fluids into the fluid conduit 530 at step 802, the second fluid is pressurized at step 804 relative to a total pressure of all the fluid within the fluid conduit 530. Pressurizing the second fluid in the second fluid reservoir 500b may include advancing the second drive component 510b to oppose the pressure of the fluid in the fluid conduit 530 and thereby prevent backflow of the fluid in the fluid conduit 530 towards the second fluid reservoir 500b. The desired steady-state ratio of the first fluid and the second fluid in the second phase of the injection protocol is reached at a quicker rate than if the second drive component 510b was not actuated to pressurize the second fluid reservoir 500b prior to transitioning to the second phase of the injection protocol (see, e.g., FIGS. 5-8). Actuating the second drive component 510b to pressurize the second fluid reservoir 500b may be controlled by the at least one processor 440.

In some aspects or examples, pressurizing the second fluid relative to the pressure of the first fluid includes selecting a pressure ratio of the pressure of the first fluid and a pressure of the second fluid to reach the desired steady-state flow ratio of the first fluid and the second fluid for the second phase of the injection protocol. In some aspects or examples, pressurizing the second fluid relative to the pressure of the first fluid includes gradually increasing the pressure of the second fluid such that at the transition from the first phase of the injection protocol to the second phase of the injection protocol, the pressure of the second fluid in the second fluid reservoir 500*b* is substantially equal to the pressure of the first fluid in the fluid conduit 530. In other aspects or examples, pressurizing the second fluid relative to the pressure of the first fluid may include gradually increasing a pressure of the second fluid such that, at the transition from the first phase of the injection protocol to the second phase of the injection protocol, the pressure of the second fluid in the second fluid reservoir 500*b* is 20% to 150% of the pressure of the first fluid in the fluid conduit 530. In addition to obtaining more accurate fluid flow profiles, the present disclosure may also prevent backflow from the higher pressure syringe into the lower pressure syringe, which can occur where there is a difference in pressure between the syringes (see, PCT International Application No. PCT/US2019/048249, filed Aug. 27, 2019 entitled "Fluid Injector System, Method of Preventing Fluid Backflow, and Computer Program Product", the disclosure of which is incorporated herein by reference.

With continued reference to FIG. 12, the method 800 further may include, at step 806, during the second phase of the injection protocol, actuating the second of the drive component 510*b* to inject the second fluid from the second fluid reservoir 500*b* through the fluid conduit 530 so that the desired steady-state ratio of the first fluid and the second fluid in the second phase is reached. In some aspects or examples, the second phase of the injection protocol includes the first fluid in addition to the second fluid, in which case the first drive component 510*a* is actuated, or remains actuated following the first phase, to pressurize and inject the first fluid from the first fluid reservoir 500*a*. In some aspects or examples, step 806 further includes adjusting a speed of the first drive component 510*a* to inject the first fluid at a desired flow rate to reach the desired steady-state ratio of the first fluid and the second fluid through the fluid conduit 530 during the second phase of the injection protocol. That is, the speed of the first drive component 510*a* may be adjusted to transition from the desired steady-state ratio of the first phase of the injection protocol to the desired steady-state ratio of the second phase of the injection protocol.

It will be understood by one of skill in the art that similar protocols and methods may include a third or more fluids that may be included in the fluid flow to reach steady-state without deviating from the scope of the present disclosure. Additional fluids prescribed in the second phase of the injection protocol may be pressurized and injected from the additional fluid reservoirs 500*n* by actuating the associated additional drive components 510*n*. Actuating any of the drive components 510*a*, 510*b*, 510*n* may include distally advancing the drive component 510*a*, 510*b*, 510*n* to reduce the internal volume of the associated fluid reservoir 500*a*, 500*b*, 500*n*. The drive components 510*a*, 510*b*, 510*n* may be advanced at a constant speed, at a linearly increasing or decreasing speed, at an exponentially increasing or decreasing speed, or any other speed profile, including, for example a pulsed speed profile. Actuation of the drive components 510*a*, 510*b*, 510*n* may be controlled by the at least one processor 440.

In aspects or examples in which the fluid injector system 100 is a closed system, the method 800 further may include closing the second valves 520*b* prior pressurizing the second fluid reservoir 500*b* at step 804 to prevent flow from the fluid conduit 530 into the second fluid reservoir 500*b*. Further, closing of the second valve 520*b* prior to pressurizing the second fluid reservoir 500*b* at step 804 may also reduce the volume and pressure effects due to compliance volume of the second fluid reservoir 500*b* and system slack associated with the second drive component 510*b*. In some aspects or examples, the second valve 520*b* may be closed prior to injecting the first phase of the injection protocol at step 802. With the second valve 520*b* closed, the second fluid reservoir 500*b* is isolated from the fluid conduit 530 and the other fluid reservoirs 500*a*, 500*n*. As such, backflow of the first fluid into the second fluid reservoir 500*b* is prevented. During the transition to the second phase of the injection protocol at step 806, the second valve 520*b* may be at least partially opened to allow the second fluid from the second fluid reservoir 500*b* to be injected into the fluid conduit 530. When the second valve 520*b* is opened, the pressure generated in the second fluid reservoir 500*b* at step 804 may overcome the pressure of the fluid previously injected into the fluid conduit 530 (at step 802), allowing the second fluid to advance into the fluid conduit 530 and mix with the first fluid without having to overcome the pressure differential of the pressurized first fluid and the compliance effects from pressurizing the second fluid reservoir 500*b*, thereby reducing the time required to reach the desired steady-state ratio and desired flow profile for the first fluid and the second fluid of the second phase of the injection protocol.

Referring now to FIG. 13, another method for reducing the time required to reach the desired steady-state ratio of the second phase of the injection protocol is shown. At step 902 the method 900 may include, during the first phase of the injection protocol, actuating one or more of the drive components 510*a*, 510*b*, 510*n* to inject at least one fluid from the one or more fluid reservoirs 500*a*, 500*b*, 500*n* through the fluid conduit 530 at the desired steady-state ratio for the first phase of the injection protocol. Actuating any of the drive components 510*a*, 510*b*, 510*n* may include distally advancing the drive component 510*a*, 510*b*, 510*n* to reduce the internal volume of the associated fluid reservoir 500*a*, 500*b*, 500*n*. The drive components 510*a*, 510*b*, 510*n* may be advanced at a constant speed, at a linearly increasing or decreasing speed, at an exponentially increasing or decreasing speed, or any other speed profile. Actuation of the drive components 510*a*, 510*b*, 510*n* may be controlled by the at least one processor 440.

In aspects or examples in which the fluid injector system 100 is a closed system, the method 900 further may include closing the second valve 520*b* prior to step 902 to prevent flow from the fluid conduit 530 into the second fluid reservoir 500*b*.

With continued reference to FIG. 13, the method 900 further may include, at step 904, during an initial portion of the second phase of the injection protocol, actuating the first and second drive component 510*a*, 510*b* to inject the first fluid and the second fluid through the fluid conduit 530 such that a ratio of volume of the second fluid displaced from the second fluid reservoir 500*b* relative to volume of the first fluid displaced from the first fluid reservoir 500*a* exceeds the desired steady-state ratio (for example as a modified steady-state volumetric ratio) and desired flow profile for the first fluid and the second fluid for the second phase. For example, is the desired steady-state ratio for the second phase is includes 10% of the second fluid to 90% of the first fluid, the first and second drive component 510*a*, 510*b* may be actuated by the at least one processor 440 to generate a ratio of 20% of the second fluid to 80% of the first fluid. The increase in the ratio of the second fluid relative to the first fluid assists the second fluid in overcoming the pressure of the first fluid flowing through the fluid conduit 530, thereby further decreasing the time required to reach the desired steady-state ratio and desired flow profile for the first fluid and the second fluid of the second phase of the injection protocol. Thus, the desired steady-state ratio of the first fluid and the second fluid in the second phase is reached more quickly than if the first and second drive component 510a, 510b were actuated such that a ratio of volume of the second fluid displaced from the second fluid reservoir 500b relative to volume of the first fluid displaced from the first fluid reservoir 500a did not exceed the desired steady-state ratio of the second phase. In certain embodiments, the modified steady-state volumetric ratio of the minor fluid of the dual flow system may range from 1.1 times the desired ratio component for the minor fluid up to 5.0 times the desired ratio component for the minor fluid.

In aspects or examples in which the fluid injector system 100 is a closed system, the method 900 further may include opening the second valve 520b prior to step 904 to allow flow from the second fluid reservoir 500b into the fluid conduit 530.

With continued reference to FIG. 13, the method 900 further may include, at step 906, subsequent to the initial portion of the second phase, actuating the first and second drive component 510a, 510b to reduce the volumetric ratio of the second fluid relative to the first fluid injected at step 904 until the volumetric ratio reaches the second desired steady-state ratio and desired flow profile for the first fluid and the second fluid in the second phase. That is, after the initial injection of the first fluid and the second fluid at the modified volumetric ratio of step 804, the ratio of the first fluid and the second fluid is adjusted to the desired steady-state ratio of the second phase. In certain embodiments, the adjustment to the desired steady-state ratio may be performed gradually over time to smoothly adjust the ratio of fluid delivered to the patient towards the desired steady-state ratio of the second phase. According to other embodiments, the adjustment to the desired steady-state ratio may be quickly adjusted after a set period of time. Appropriate modified steady-state volumetric ratios for a desired steady-state ratio of a specific phase or a specific injection protocol may be stored in a memory associated with the controller, such as in a "look-up table", or may be determined by one or more algorithmic calculation.

In some aspects or examples, the method 900 further may include, during the first phase of the injection protocol prior to transitioning to the second phase of the injection protocol, actuating the second drive component 510b to pressurize the second fluid in the second fluid reservoir 500b relative to a pressure of the first fluid injected into the fluid conduit 530. Pressurizing the second fluid may be performed in same manner as described herein with reference to step 804 of the method 800. In aspects or examples in which the fluid injector system 100 is a closed system, the method 900 further may include closing the second valve 520b prior to pressurizing the second fluid reservoir 500b. With the second valve 520b closed, the second fluid reservoir 500b is isolated from the fluid conduit 530 and the other fluid reservoirs 500a, 500n. As such, backflow into the second fluid reservoir 500b is prohibited. During the transition to the second phase of the injection protocol at step 906, the second valve 520b may be opened to allow the second fluid from the second fluid reservoir 500b to be injected into the fluid conduit 530. When the second valve 520b is opened, the pressure generated in the second fluid reservoir 500b may overcome the pressure of the fluid previously injected into the fluid conduit 530 (at step 902), allowing the second fluid to advance into the fluid conduit 530 and reducing the time required to reach the desired steady-state ratio of the second phase of the injection protocol.

In some aspects or examples, the methods 800, 900 further may include, during the first phase of the injection protocol prior to transitioning to the second phase of the injection protocol, ceasing actuation or reducing the speed of the first drive component 510a to reduce the pressure of the first fluid in the fluid conduit 530. Due to the cessation of speed reduction of the first drive component 510a, the fluid pressure within the fluid conduit 530 is temporarily reduced at the start of the second phase of the injection protocol. Consequently, the second fluid injected into the fluid conduit 530 at the beginning of the second phase must only overcome the reduced pressure of the first fluid in the fluid conduit 530, allowing the desired steady-state ratio of the second phase of the injection protocol to be reached more quickly than if the first drive component 510a was not reduced in speed. Once the second fluid has begun flowing into the fluid conduit 530, the speed of the first drive component 510a may be returned to the speed prescribed by the injection protocol to achieve the desired steady-state ratio of the second phase.

In some aspects or examples, the methods 800, 900 further may include, during the first phase of the injection protocol prior to transitioning to the second phase of the injection protocol, adjusting at least one property of the injection protocol to prevent backflow of the fluid from the fluid conduit 530 towards the second fluid reservoir 500b. In some aspects or examples, adjusting at least one property of the injection protocol may include pulsing the second drive component 510b to generate a pressure front within the fluid conduit 530 that prevents the fluid in the fluid conduit 530 from flowing toward the second fluid reservoir 500b. Exemplary processes and methods for pulsing the second drive component 510b are described in PCT International Application No. PCT/US2019/048249.

Figure 9:
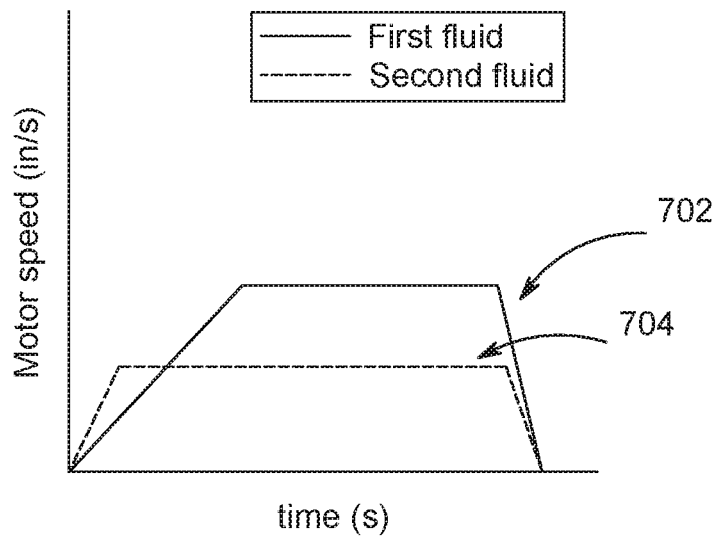
FIG. 9 is a graph showing a relationship of a drive speed profile of a first drive component and a second drive component as a function of time according to one example of the present disclosure.
Figure 10:
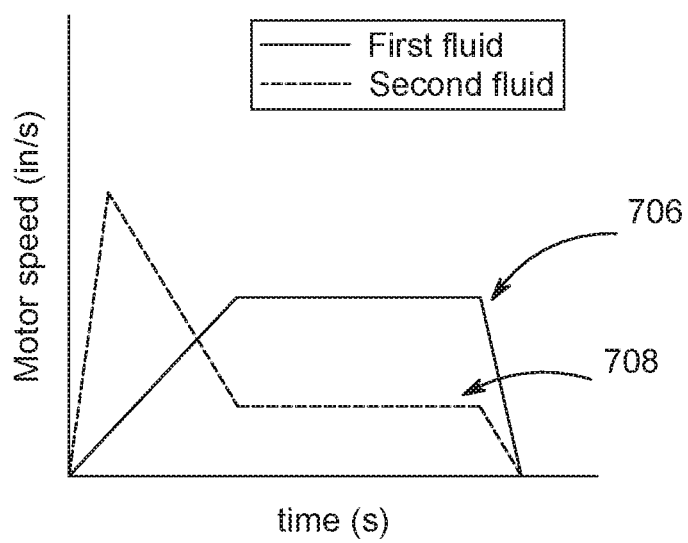
FIG. 10 is a graph showing a relationship of a drive profile of a first drive component and a second drive component as a function of time according to another example of the present disclosure.
Figure 11:
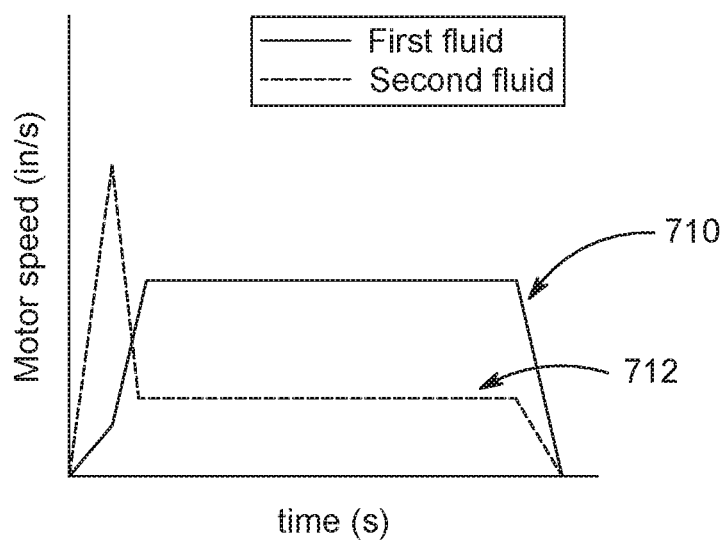
FIG. 11 is a graph showing a relationship of a drive profile of a first drive component and a second drive component as a function of time according to another example of the present disclosure.

In some aspects or examples, adjusting at least one property of the injection protocol may include advancing one or more of the drive components 510a, 510b, 510n at a constant speed, linearly increasing the speed of one or more of the drive components 510a, 510b, 510n, and/or exponentially increasing the speed of one or more of the drive components 510a, 510b, 510n. FIGS. 9-11 illustrate various motor speed profiles for the first and second drive component 510a, 510b during the second phase of the injection protocol. Referring first to FIG. 9, a motor speed profile 702 for the first drive component 510a is compared to a motor speed profile 704 for the second drive component 510b. As can be appreciated from FIG. 9, both of the motor speed profiles 702, 704 gradually increase from zero to a constant speed, with the constant speed corresponding to motor speed at the desired steady-state ratio of the first fluid and the second fluid. However, the motor speed profile 704 of the second fluid increases toward its constant speed at a faster rate relative to the motor speed profile 702. The result of actuating the first and second drive component 510a, 510b in accordance with the motor speed profiles 702, 704, respectively, is that the second fluid is initially delivered at a faster rate and in greater volume, thereby overcoming the pressure of the first fluid in the fluid conduit 530. As such, the desired steady-state ratio of the first fluid and the second fluid is reached more quickly than if the motor speed profiles 702, 704 increased towards their respective constant speeds at the same rate.

Similar to FIG. 9, FIGS. 10 and 11 illustrate comparisons of motor speed profiles 706, 710 for the first drive component 510*a* relative to motor speed profiles 708, 712 for the second drive component 510*b*. In both FIGS. 10 and 11, motor speed profiles 708, 712 for the second drive component 510*b* initially increase at a faster rate than motor speed profiles for the first drive component 510*a*. Additionally, motor speed profiles 708, 712 each include an initial spike during which the motor speed increases to a maximum speed above the constant speed, and the speed is subsequently decreased to the constant speed. The spikes in motor speed profiles 708, 712 enhance the effect of overcoming the pressure of the first fluid in the fluid conduit 530 to more quickly reach the desired steady-state ratio of the first fluid and the second fluid.

In some aspects and examples of a closed fluid injector system 100 (e.g., the fluid injector system 100 of FIGS. 1 and 2), the at least one processor 404 may be programmed or configured to execute an injection protocol including a single phase that is a dual flow phase including at least a first fluid delivered to the fluid conduit 530 from the first fluid reservoir 500*a* via actuation of the first drive component 510*a* and at least a second fluid delivered to the fluid conduit 530 from the second fluid reservoir 500*b* via actuation of the second drive component 510*b*. Such single phase, multi-fluid injection protocol may include or define a desired steady-state ratio of a first fluid relative to at least a second fluid. According to various embodiments, the steady-state ratio of fluids in the single phase may range from 99:1 of the first fluid to the second fluid to 1:99 of the first fluid to the second fluid, inclusive of any intermediate ratios.

The desired steady-state ratio for the first and second fluid of the injection protocol may be reached by selectively and independently actuating the first and second drive components 510*a*, 510*b* and the first and second valves 520*a*, 520*b* associated with the first and second fluid reservoir 500*a*, 500*b* and optionally actuating a third drive component 510*n* and a third valve 520*n* associated with a third fluid reservoir 500*n*. In order to compensate for effects of one or more fluid flow factors (e.g., fluid ratio of the two or more fluids, differences in the densities and/or viscosities of the two or more fluids, system slack, impedance and/or capacitance of the two or more fluid reservoirs) affecting the desired fluid ratio, the controller 404 instructs the various drive components and valves to drive at a specific rate and open at a specific time such that the volumetric ratio of the first fluid relative to the second fluid actually delivered to the patient is substantially consistent with the programmed injection protocol.

In aspects or examples in which the fluid injector system 100 is a closed system, the first and second valves 510*a*, 520*b* are initially closed. The controller 404 may instruct the first drive component 510*a* to pressurize the first fluid in the first fluid reservoir 500*a* to a first pressure and a instruct the second drive component 510*b* to pressurize the second fluid in the second fluid reservoir 500*b* to a second pressure. During pressurizing of the first and second fluid reservoirs 500*a*, 500*b*, the first and second fluids are isolated from the fluid conduit 530 due to the closed state of the first and second valves 520*a*, 520*b*. Depending on the fluid flow factors, the first pressure may be lower, substantially equal to, or higher than the second pressure. In some aspects or examples, pressurizing the second fluid relative to the pressure of the first fluid includes selecting a pressure ratio of the pressure of the first fluid and a pressure of the second fluid to reach the desired initial flow ratio that matches the desired steady-state flow ratio of the first fluid and the second fluid.

Upon reaching the desired first and second pressure, the first and second valves 520*a*, 520*b* are opened and actuation of the first and second drive components 510*a*, 510*b* is continued, thereby allowing the pressurized first and second fluids to be delivered from the first and second reservoirs 500*a*, 500*b* to the fluid conduit 530 through the first and second valves 520*a* 520*b*. The first and second drive components 510*a*, 510*b* may be advanced at a constant speed, at a linearly increasing or decreasing speed, at an exponentially increasing or decreasing speed, or any other speed profile. Actuation speed of the first and second drive components 510*a*, 510*b* prior to opening the first and second valves 520*a*, 520*b* may increase, decrease, or remain the same as the actuation speed after opening of the first and second valves 520*a*, 520*b*. The desired steady-state ratio of the first fluid and the second fluid is reached at a quicker rate than if the first and second drive components 510*a*, 510*b* were not actuated to pressurize the first and second fluid reservoirs 500*a* 500*b*.

It will be understood by one of skill in the art that similar protocols and methods may include a third or more fluids that may be included in the fluid flow to reach steady-state without deviating from the scope of the present disclosure. Additional fluids prescribed in the second phase of the injection protocol may be pressurized and injected from the additional fluid reservoirs 500*n* by actuating the associated additional drive components 510*n* and additional valves 520*n*. As described herein, actuation of the drive components 510*a*, 510*b*, 510*n* and valves 520*a*, 520*b*, 520*n* may be controlled by the at least one processor 440.

While examples of fluid injector systems, methods of operation thereof, and computer program products were provided in the foregoing description, those skilled in the art may make modifications and alterations to these examples without departing from the scope and spirit of the disclosure. Accordingly, the foregoing description is intended to be illustrative rather than restrictive. The disclosure described hereinabove is defined by the appended claims, and all changes to the disclosure that fall within the meaning and the range of equivalency of the claims are to be embraced within their scope.

We claim:

1. A fluid injector system configured to perform an injection protocol comprising at least a first phase and a second phase, the second phase subsequent to the first phase, the fluid injector system comprising:
 a control device operatively associated with a first drive component and a second drive component, the first drive component configured to pressurize and inject a first fluid from a first fluid reservoir through a fluid conduit, the second drive component configured to pressurize and inject a second fluid from a second fluid reservoir through the fluid conduit, and at least a first valve configured to control fluid communication between the first fluid reservoir and the fluid conduit and a second valve configured to control fluid communication between the second fluid reservoir and the fluid conduit, the first valve and the second valve controlled by at least one processor of the control device between an open position and a closed position,
 wherein the at least one processor is programmed or configured to:
   during the first phase of the injection protocol, actuate at least the first drive component to inject the first fluid through the fluid conduit and operate the second valve to the closed position;

during the first phase of the injection protocol prior to transitioning to the second phase of the injection protocol, actuate the second drive component and maintain the second valve in the closed position to pressurize the second fluid relative to a pressure of the first fluid in the fluid conduit, wherein pressurizing of the second fluid relative to the pressure of the first fluid comprises selecting a pressure ratio of the pressure of the first fluid and a pressure of the second fluid to reach a desired steady-state flow ratio of the first fluid and the second fluid for the second phase of the injection protocol; and during the second phase of the injection protocol, operate the second valve to the open position and actuate the second drive component to inject at least the second fluid through the fluid conduit so that the desired steady-state ratio of the first fluid and the second fluid in the second phase of the injection protocol is reached.

2. The fluid injector system of claim 1, wherein the desired steady-state ratio of the first fluid and the second fluid in the second phase of the injection protocol is reached at a quicker rate than if the second drive component is not actuated prior to the transitioning to the second phase of the injection protocol.

3. The fluid injector system of claim 1, wherein the at least one processor is further programmed or configured to: during the first phase of the injection protocol prior to the transitioning to the second phase of the injection protocol, cease actuation or reduce a speed of the first drive component.

4. The fluid injector system of claim 1, wherein the at least one processor is further programmed or configured to: during the second phase of the injection protocol, adjust a speed of the first drive component to inject the first fluid at a flow rate to reach the desired steady-state ratio of the first fluid and the second fluid through the fluid conduit.

5. The fluid injector system of claim 1, wherein the pressurizing of the second fluid relative to the pressure of the first fluid comprises gradually increasing the pressure of the second fluid such that during the transitioning to the second phase of the injection protocol from the first phase of the injection protocol, the pressure of the second fluid is substantially equal to the pressure of the first fluid.

6. The fluid injector system of claim 1, wherein the at least one processor is further programmed or configured to; during the first phase of the injection protocol prior to the transitioning to the second phase of the injection protocol, adjust at least one property of the injection protocol to prevent backflow of the first fluid into the second fluid reservoir.

7. The fluid injector system of claim 6, wherein the adjusting of at least one property of the injection protocol comprises at least one of: advancing the second drive component at a constant speed, linearly increasing a speed of the second drive component, and exponentially increasing the speed of the second drive component.

8. A method of performing an injection protocol comprising at least a first phase and a second phase using a fluid injector system, the second phase subsequent to the first phase, the method comprising:

providing a control device of the fluid injector system operatively associated with a first drive component and a second drive component of the fluid injector system, the first drive component configured to pressurize and inject a first fluid from a first fluid reservoir through a fluid conduit, the second drive component configured to pressurize and inject a second fluid from a second fluid reservoir through the fluid conduit, and at least a first valve of the fluid injector system configured to control fluid communication between the first fluid reservoir and the fluid conduit and a second valve of the fluid injector system configured to control fluid communication between the second fluid reservoir and the fluid conduit, the first valve and the second valve controlled by at least one processor of the control device between an open position and a closed position;

actuating at least the first drive component to inject the first fluid through the fluid conduit and operating the second valve to the closed position during the first phase of the injection protocol;

actuating the second drive component and maintaining the second valve in the closed position to pressurize the second fluid relative to a pressure of the first fluid in the fluid conduit during the first phase of the injection protocol prior to transitioning to the second phase of the injection protocol, wherein pressurizing of the second fluid relative to the pressure of the first fluid comprises selecting a pressure ratio of the pressure of the first fluid and a pressure of the second fluid to reach a desired steady-state flow ratio of the first fluid and the second fluid for the second phase of the injection protocol; and operating the second valve to the open position and actuating the second drive component to inject at least the second fluid through the fluid conduit so that the desired steady-state ratio of the first fluid and the second fluid in the second phase is reached during the second phase of the injection protocol.

9. The method of claim 8, wherein the desired steady-state ratio of the first fluid and the second fluid in the second phase of the injection protocol is reached at a quicker rate than if the second drive component is not actuated prior to the transitioning to the second phase of the injection protocol.

10. The method of claim 8, further comprising ceasing actuation or reducing a speed of the first drive component during the first phase of the injection protocol prior to the transitioning to the second phase of the injection protocol.

11. The method of claim 8, further comprising adjusting a speed of the first drive component to inject the first fluid at a flow rate to reach the desired steady-state ratio of the first fluid and the second fluid through the fluid conduit during the second phase of the injection protocol.

12. The method of claim 8, wherein pressurizing the second fluid relative to the pressure of the first fluid comprises gradually increasing the pressure of the second fluid such that, during the transitioning to the second phase of the injection protocol from the first phase of the injection protocol, the pressure of the second fluid is substantially equal to the pressure of the first fluid.

13. The method of claim 8, further comprising adjusting at least one property of the injection protocol to prevent backflow of the first fluid into the second fluid reservoir during the first phase of the injection protocol prior to the transitioning to the second phase of the injection protocol.

14. The method of claim 13, wherein the adjusting of at least one property of the injection protocol comprises at least one of: advancing the second drive component at a constant speed, linearly increasing a speed of the second drive component, and exponentially increasing the speed of the second drive component.

* * * * *

UNITED STATES PATENT AND TRADEMARK OFFICE
CERTIFICATE OF CORRECTION

PATENT NO. : 12,427,249 B2
APPLICATION NO. : 17/270616
DATED : September 30, 2025
INVENTOR(S) : Chaya et al.

It is certified that error appears in the above-identified patent and that said Letters Patent is hereby corrected as shown below:

In the Specification

In Column 23, Line 57, delete "do to" and insert -- due to --, therefor.
In Column 28, Line 7, delete "fluid," and insert -- fluid. --, therefor.
In Column 29, Line 22, delete "2019" and insert -- 2019) --, therefor.
In Column 30, Line 1, delete "prior pressurizing" and insert -- prior to pressurizing --, therefor.
In Column 30, Line 64, delete "is the" and insert -- if the --, therefor.
In Column 30, Line 64, delete "phase is" and insert -- phase --, therefor.
In Column 34, Line 22, delete "500a 500b." and insert -- 500a, 500b. --, therefor.

In the Claims

In Column 35, Line 48, in Claim 6, delete "configured to;" and insert -- configured to: --, therefor.

Signed and Sealed this
Twenty-fifth Day of November, 2025

John A. Squires
*Director of the United States Patent and Trademark Office*